United States Patent
Kingston et al.

(10) Patent No.: US 7,312,240 B2
(45) Date of Patent: Dec. 25, 2007

(54) CONFORMATIONALLY CONSTRAINED PACLITAXEL ANALOGS AND THEIR USE AS ANTICANCER AND ANTI-ALZHEIMERS AGENTS

(75) Inventors: David George Ian Kingston, Blacksburg, VA (US); Thota Ganesh, Blacksburg, VA (US); James Patrick Synder, Atlanta, GA (US); Ami S. Lakdawala, Philadelphia, PA (US); Susan Lynn Bane, Vestal, NY (US)

(73) Assignees: Virginia Tech Intellectual Properties, Inc., Blacksburg, VA (US); Binghamton University, Binghamton, NY (US); Emory University, Atlanta, GA (US)

( * ) Notice: Subject to any disclaimer, the term of this patent is extended or adjusted under 35 U.S.C. 154(b) by 314 days.

(21) Appl. No.: 11/035,037

(22) Filed: Jan. 14, 2005

(65) Prior Publication Data

US 2005/0187287 A1    Aug. 25, 2005

Related U.S. Application Data

(60) Provisional application No. 60/536,247, filed on Jan. 14, 2004.

(51) Int. Cl.
*A01N 43/02* (2006.01)
*A61K 31/335* (2006.01)

(52) U.S. Cl. .................................................... 514/449
(58) Field of Classification Search ................. 514/449
See application file for complete search history.

(56) References Cited

OTHER PUBLICATIONS

Freshnet et al., Culture of animal cells, A manual of basic technique, Alan R. Liss, Inc., 1983, New York, pp. 1-6.*
Dermer et al., Bio/lechnology, 1994, 12:320.*
Liu et al., "Syntheses and bioactivities of macrocyclic paclitaxel bis-lactones", Bioorganic & Medicinal Chemistry, 2004, vol. 12, pp. 6147-6161.*
Synthesis and Biological Evaluation of Novel Macrocyclic Paclitaxel Analogues, B. Metaferia, et al. Department of Chemistry, Virginia Polytechnic Institute and State University, Blacksburg, Virginia; Organic Letters, 2001 vol. 3, No. 16; pp. 2461-2464.

* cited by examiner

*Primary Examiner*—Margaret D. Seaman
*Assistant Examiner*—Niloofar Rahmani
(74) *Attorney, Agent, or Firm*—Whitham Curtis Christofferson & Cook, PC

(57) ABSTRACT

Constrained paclitaxel derivatives include a bridge extending from the C-3' phenyl to either the C4 or -3 positions. Many of the constrained paclitaxel derivatives provide activity comparable or superior to the natural product paclitaxel.

5 Claims, 15 Drawing Sheets

1a R[1] = Ph, R[2] = Ac
1b R[1] = Me₃CO, R[2] = H

| Entry | Baccatin | β-lactam | Taxoid-w,w-diene | yield |
|---|---|---|---|---|
| 1 | 11a | 7a | 12a, R=TES, R₁=TIPS; 13a, R=R₁=H | 12a: (65%)<br>13a: (55%) |
| 2 | 11a | 7b | 12b, R=TES, R₁=TIPS; 13b, R=R₁=H | 12b: (83%)<br>13b: (71%) |
| 3 | 11a | 7c | 12c, R=TES, R₁=TIPS; 13c, R=R₁=H | 12c: (50%)<br>13c: (70%) |
| 4 | 11a | 7d | 12d, R=TES, R₁=TIPS; 13d, R=R₁=H | 12d: (50%)<br>13d: 100% |
| 5 | 11a | 7f | 12e, R=TES, R₁=TIPS; 13fe, R=R₁=H | 12e: (66%)<br>13e: (83%) |
| 6 | 11a | 7g | 12f, R=TES, R₁=TIPS; 13f, R=R₁=H | 12f: (87%)<br>13f: (0%) |

*Figure 7A*

| Entry | Baccatin | β-lactam | Taxoid-w,w-diene | yield |
|---|---|---|---|---|
| 7 | 11b | 7a | 12g, R=TES, R₁=TIPS; 13g, R=R₁=H | 12g: (70%)<br>13g: (50%) |
| 8 | 11b | 7b | 12h, R=TES, R₁=TIPS; 13h, R=R₁=H | 12h: (57%)<br>13h: (95%) |
| 9 | 11b | 7c | 12i, R=TES, R₁=TIPS; 13i, R=R₁=H | 12i: (66%)<br>13i: (69%) |
| 10 | 11c | 7c | 12j, R=TES, R₁=TIPS; 13j, R=R₁=H | 12j: (82%)<br>13j: (68%) |
| 11 | 11d | 7c | 1kl, R=TES, R₁=TIPS | 12k: (65%) |

Figure 7B

| Entry | ω,ϖ-diene | macrocyclic product | Yield % | Isomer |
|---|---|---|---|---|
| 1 | 12a | b ⎰14a: R=TES, R₁=TIPS<br>c ⎱15a: R=R₁=H<br>   ⎱16a: Dihydro 15a | 14a: 65<br>15a: 99<br>16a: 87 | E |
| 2 | 12c | b ⎰14b: R=TES, R₁=TIPS<br>c ⎱15b: R=R₁=H<br>   ⎱16b: Dihydro 15b | 14b: 64<br>15b: 98<br>16b: 96 | E |
| 3 | 12d | b ⎰14c: R=TES, R₁=TIPS<br>c ⎱15c: R=R₁=H<br>   ⎱16c: Dihydro 15c | 14c: 91<br>15c: 100<br>16c: 88 | E/Z (3:1) |
| 4 | 12f | b ⎰14d: R=TES, R₁=TIPS<br>c ⎱15d: R=R₁=H<br>   ⎱16d: Dihydro 15d | 14d: 87<br>15d: 77<br>16d: 62 | Z |
| 5 | 12g | b ⎰14e: R=TES, R₁=TIPS<br>c ⎱15e: R=R₁=H<br>   ⎱16e: Dihydro 15e | 14e: 85<br>15e: 75<br>16e: 66 | Z |

Figure 8A

| Entry | ω,ϖ-diene | macrocylic product | Yield % | Isomer |
|---|---|---|---|---|
| 6 | 12h | (structure) b ⎰14f: R=TES, R₁=TIPS  ⎱15f: R=R₁=H  c ⎰16f: Dihydro 15f | 14f: 82  15f: 70  16f: 87 | Z |
| 7 | 12i | (structure) b ⎰14g: R=TES, R₁=TIPS  ⎱15g: R=R₁=H  c ⎰16g: Dihydro 15g | 14g: 65  15g: 98  16g: 87 | E/Z (5:1) |
| 8 | 12j | (structure) b ⎰14h: R=TES, R₁=TIPS  ⎱15h: R=R₁=H  c ⎰16h: Dihydro 15h | 14h: 60  15h: 78  16h: 65 | E/Z (5:1) |
| 9 | 12k | (structure) b ⎰14i: R=TES, R₁=TIPS  ⎱15i: R=R₁=H | 14i: 55  15i: 67 | E/Z (3:1) |
| 10 | 12f | (structure) b ⎰14J: R=TES, R₁=TIPS  ⎱15J: R=R₁=H  c ⎰16J: Dihydro 15J | 14J: 75  15J: 77  16J: 70 | E |

Figure 8B

| Bridge taxoids | IC$_{50}$ values (nM) | | |
|---|---|---|---|
| | 1A9 | PTX10 | A8 |
| PTX | 8.0 | 157 | 28.7 |
| 15b | 7.6 | 126 | 28.7 |
| 15c | 17.1 | 157 | 56 |
| 15d | 0.072 | 0.13 | 0.32 |
| 15e | 30.9 | 196 | >300 |
| 15f | 7.6 | 157 | >300 |
| 16b | 19.8 | 35.9 | 70 |
| 16d | 0.083 | 1.03 | 0.57 |

\#: 1A9 and PTX10 are the paclitaxel resistant cell lines and A8 is the epothilone A resistant cell line which is also cross resistant to paclitaxel (5-10 times).

*Figure 9* i. HF-pyridine, 12h, 75-77%. ii.CDCl₃, 5 days, RT 75% a. (Cy₃P)₂Ru=CHPh, or (I Mes)(Cy₃)P)Ru=CHPh,DCM, RT-55 C,
b. Same catalyst as in a, tolune 80°C

CONFORMATIONALLY CONSTRAINED PACLITAXEL ANALOGS AND THEIR USE AS ANTICANCER AND ANTI-ALZHEIMERS AGENTS This application claims priority to U.S. Provisional Application 60/536,247 filed Jan. 14, 2004, the entire contents of which is hereby incorporated by reference.

This invention was made using funds from a grant from the National Institutes of Health having grant number CA-69571. The United States government may have certain rights in this invention.

BACKGROUND OF THE INVENTION

1. Field of the Invention

The present invention generally relates to paclitaxel derivatives and, more particularly, paclitaxel derivatives that are conformationally constrained.

2. Background Description

Paclitaxel (PTX or "Taxol™") is a natural product and is the world's leading anticancer drug. With reference to FIG. 1, PTX (1a) and its closely related, semi-synthetic, analog docetaxel (1b) are clinically approved drugs for several tumor malignancies. These molecules, including several other newly discovered natural products (e.g., epothilones, discodermolide and eleutherobin), induce apoptotic cell death by promoting polymerization of tubulin to microtubules and their stabilization. Significant advances have been made since the discovery and publication of the electronic crystallographic 3.7 Angstrom zinc induced tubulin structure (see, Nogales, et al., *Nature*, 391:199-203 (1998). This model, however, lacks the resolution to define the paclitaxel three-dimensional interaction on tubulin polymer.

Paclitaxel is a complex molecule and is expensive to produce in large quantities. A clear understanding of the three dimensional interaction of PTX in the binding site on the tubulin receptor would be beneficial for the rational design of new generation drugs. There has been ample evidence available from 2D NMR analysis and modeling studies to support the three bioactive models proposed for PTX. The polar (extended) conformation with clustering of C-2 benzoate and C-3'-benzamide side chain was proposed as a bioactive conformer. Similarly, several reports appeared in favor of a hydrophobic collapse conformation clustering of C-2 benzoate and the C-3' phenyl group. The hydrophobic collapse conformation was also proposed by the inventors of the present invention based upon the combination of fluorescent spectroscopy using FRET measurements and REDOR NMR studies. However, none of the conformationally constrained analogs synthesized to date, based on any of the above models, resulted in equal or more active PTX analogs than the parent compound itself. In most cases they were inactive, and in some cases they exhibited 2-30 fold less bioactivity, with respect to PTX.

Given the significant advantages of PTX and related compounds in patient care for a wide range of disorders (human cancers including breast, ovarian, and lung cancer; neurodegenerative disorders such as Alzheimer's disease, etc.), it would be beneficial to have alternative derivatives that are as active or more active, or that are easier to mass produce.

SUMMARY OF THE INVENTION

This invention describes the synthesis of a new class of paclitaxel (Taxol™) analogs ("derivatives") which are as active as paclitaxel against two different cancer cell lines and are also more active than paclitaxel as tubulin-polymerization agents. The general structure of these analogs includes a bridge from the C-3' phenyl group to either the C-3 or C-4 position. This bridge constrains the compound in the correct conformation to bind to its tubulin receptor. These compounds can be modified by adjusting other functional groups. Thus, the invention includes a whole new class of paclitaxel derivatives which will be active as anticancer agents (e.g., breast, ovarian, and lung cancers, etc.) and agents for use in treating neurodegenerative disorders (e.g., Alzheimer's disease, etc.).

Recently, the T-Taxol (butterfly) conformation model from deconvolution of averaged spectra of paclitaxel in chloroform has been recognized (see, Snyder et al., *J. Am. Chem. Soc.* 122:724-725 (2000)), and it has been reported as being a bioactive conformation based on its fit into the electronic crystallographic density (see, Snyder et al., *Proc. Natl. Acad. Sci. USA* 98:5312-5316 (2001)). This model explicitly relates the C-2 benzoate group of PTX, positions equidistant from the phenyl and benzamide groups emanating from the C-3' position, resulting in a T-shaped conformation. This model also explains that when the T-taxol conformation is nestled in the electron crystallographic density of the more refined PTX-tubulin complex, the His-229 residue of the protein is interposed between C-3' and C-2 phenyl rings of PTX, preventing their hydrophobic collapse.

Based on these reports, it was hypothesized that the C3'-phenyl and C4-OAc are juxtaposing each other, and the conformationally constrained analogs envisioned between these two positions should yield bioactive PTX analogs ("paclitaxel derivatives"). Further, it was concluded that the taxoid design and synthesis based on polar and nonpolar (hydrophobically collapsed) motifs are less likely to yield active compounds. In a broad spectrum synthetic program, experiments were carried out to test the T-Taxol (butterfly) model as a bioactive conformation by synthesizing a wide variety of new, conformationally constrained analogs with a tether connection between the C-4 OAc and the ortho position of the C-3' phenyl group of PTX that mimic T-taxol. In earlier experiments (see Metaferia et al. *Org. Lett.* 3:2461-2464 (2001) it was shown that a linker between the C-4 Oac and the meta position of the C-3' phenyl group yielded derivatives that were less active than PTX.

Several novel macrocyclic taxoid analogs have been synthesized and are described herein. Some of them were equal, and others are 10 to 15-fold more cytotoxic and about 1.5 times more tubulin polymerizing than PTX. These analogs are the first to provide experimental evidence of the T-Taxol conformation as a bioactive conformation of PTX. These paclitaxel derivatives can be used to treat the same disorders as paclitaxel; however, due to their unique constrained configuration, they will provide significant advantages relative to paclitaxel.

BRIEF DESCRIPTION OF THE DRAWINGS

The foregoing and other objects, aspects and advantages will be better understood from the following detailed description of a preferred embodiment of the invention with reference to the drawings, in which:

FIG. 7 presents a table of molecules in the synthesis of taxoid ω,ω' dienes.
FIG. 8 presents a table of molecules in the synthesis of macrocyclic PTX analogs.
FIG. 9 presents a table of the cytotoxicity and tubulin polymerization activity of macrocyclic taxoids and open chain paclitaxel analogs.

FIG. 18. A view of ortho-bridged 13b in which phenyl rings emanating from C-2 and C-3' surround the imidazole of His-227 in a sandwich motif; the C-4 Oac to C-3' phenyl bridge avoids the latter while stabilizing the T-Taxol conformation.

DETAILED DESCRIPTION OF THE PREFERRED EMBODIMENTS OF THE INVENTION

Figure 1:
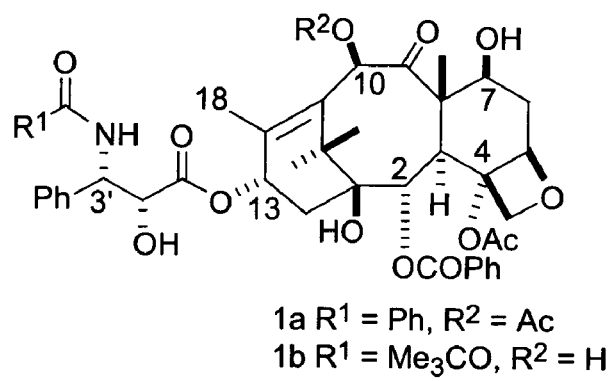
FIG. 1 is drawing of paclitaxel and docetaxel.
Figure 2:
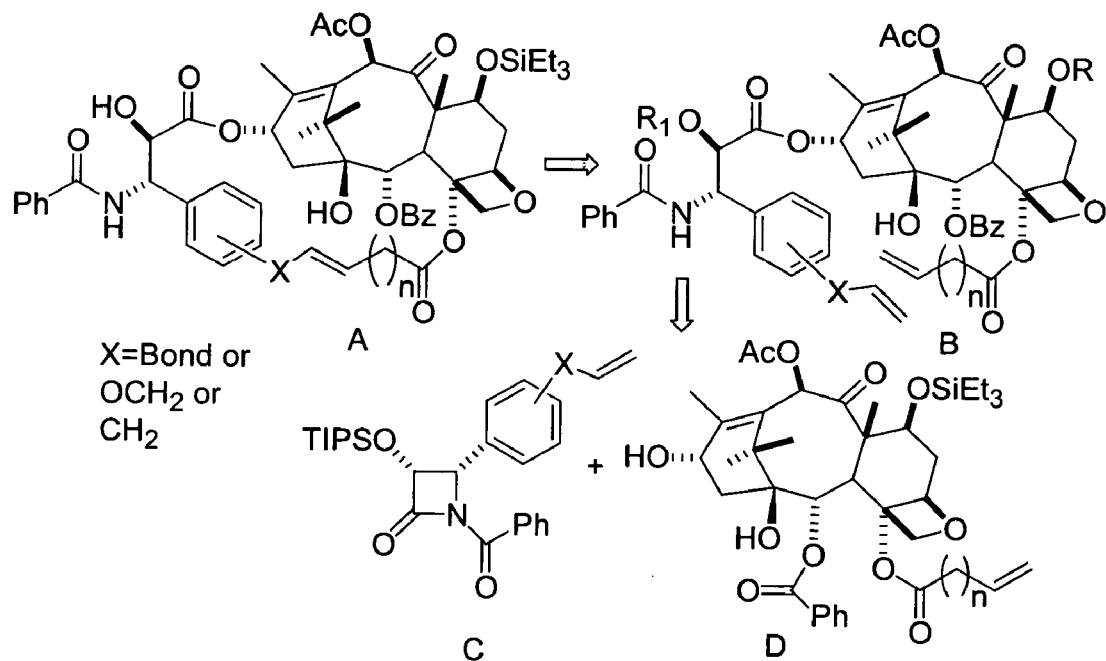
FIG. 2 is a generalized retro-synthesis route that identifies how the constrained compounds of the present invention can be made.

FIG. 2 illustrates a synthetic route which can be employed to produce the constrained PTX derivatives of the present invention. This route utilizes the ring closing metathesis (RCM) strategy (See, Trnka et al., *Acc. Chem. Res.* 34:18-29 (2001); Furstner, *Angew. Chem. Int. Ed. Engl.* 39:3012-3043 (2000); and Grubbs et al., *Tetrahedron* 54:4413-4450 (1998)) for the macrocylization step. From FIG. 2, the proposed macrocyclic analogs (A) were envisioned from the open chain taxoid ω,ω-dienes (B), which can be derived from modified β-lactams (C) and baccatin III (D) derivatives.

Figure 3:
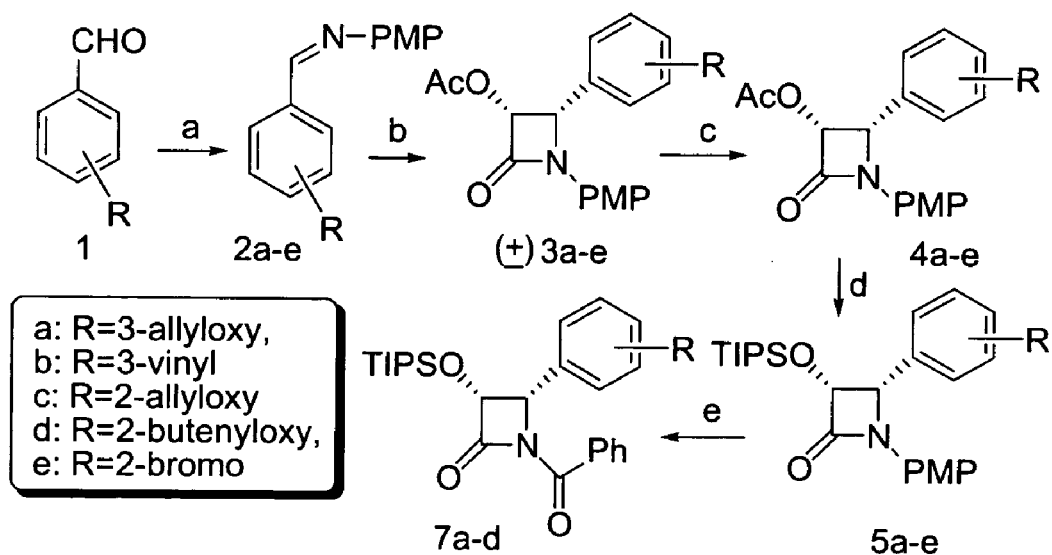
FIG. 3 illustrates synthetic scheme 1.
Figure 4:
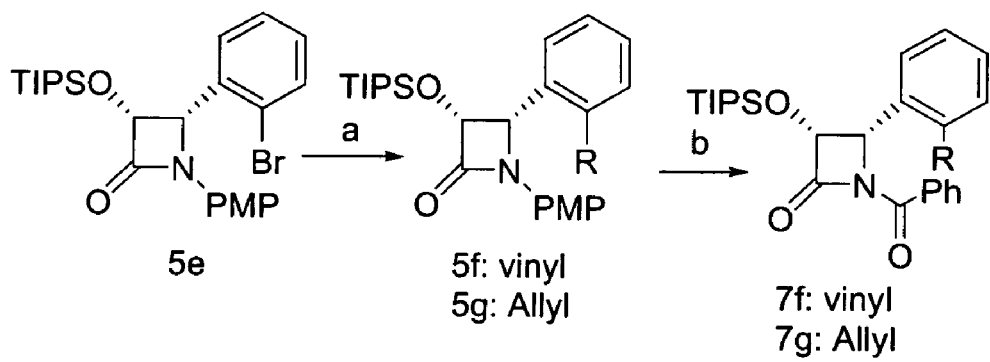
FIG. 4 illustrates synthetic scheme 2.

The retro-synthesis shown in FIG. 2 warranted several β-lactam derivatives with a tether (either from ortho or meta positions of the phenyl group) and C4 modified baccatin derivatives. The synthesis of β-lactam derivatives was achieved by procedures set forth in Scheme-1 and Scheme-2 (FIGS. 3 and 4, respectively). First, the synthesis of (±) β-lactams (3a-e) was achieved starting from 3-allyloxy, 3-vinyl, 2-allyloxy, 2-butenyl and 2-bromo benzaldehydes (1a-e) through the N-p-methoxy phenyl (PMP) protected imines 2a-e. The lipase PS (Amano) resolution of (±) β-lactams (3a-e) yielded the desired enantiomeric acetates (+)-(4a-e), along with undesired enantiomeric (−)-alcohols (not shown) in more than 95% yields. Functional group manipulations on 4a-e generated triisopropylsilyl ether intermediates 5a-e. The (4)-2-bromophenyl derivative (5e) on Stille coupling with vinyltributyltin and allyltributyltin produced the (4)-2-vinylphenyl and (4)-2-allylphenyl lactam intermediates 5f-g. All the PMP-protected intermediates 5a-g were de-protected with ceric ammonium nitrate to produce imides (6a-g, not shown), which were treated with benzoylchloride using triethylamine and dimethylaminopyridine to result in (+)-(3R,4S)-1-benzoyl-3-triisopropylsilyloxy-4-(aryl)-azetidin-2-ones (7a-g).

The reagents and conditions for Scheme 1 depicted in FIG. 3 were as follows: a. pMeOC$_6$H$_4$NH$_2$, MgSO$_4$, $_{CH2}$Cl$_2$ 100%); b. CH$_3$COOCH$_2$COCl, Et$_3$N, −78 C-RT, 12 h (80-85%); c. lipase PS Amano, phosphate bugger, pH=7.2, CH$_3$CN, 24 h-12 days (95-95%); d. i, 1M, KOH, THF, 0° C. (quantitative), ii, TIPSCI, imidazole, DMF (90-94%); e. i, CAN, CH$_3$CN, −5° C. (65-92%), ii, PhCOCl, Et$_3$N, DMAP, CH$_2$Cl$_2$ (85-95%). Scheme 2, illustrated in FIG. 4 uses the following reagents and conditions: a. Pd$_2$(dba)$_3$, Ph$_3$P, dioxane, 80° C., vinyl tributyl tin (5f, 80%), allyl tributyl tin (5g, 84%), b. (i) CAN, CH$_3$CN, −5° C. (65-70%), (ii) PhCOCl, Et$_3$N, DMAP, CH$_2$Cl$_2$ (7f, 86% and 7g, 90%).

Figure 5:
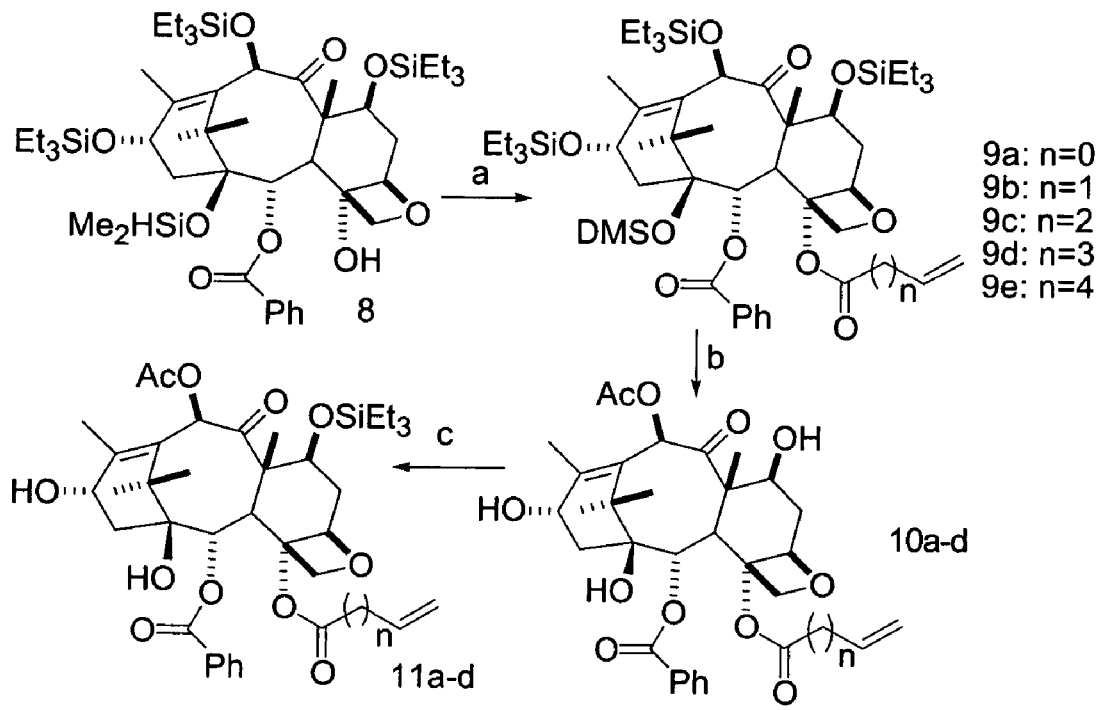
FIG. 5 illustrates synthetic scheme 3.

With reference to FIG. 5, the synthesis of baccatin derivatives (11a-d) was achieved from commercially available 10-deacetylbaccatin III (10-DAB) as starting material. The conversion of 10-DAB to C4 hydroxybaccatin derivative (8) was achieved using reported protocol. Initial attempts to acylate the hindered C-4 hydroxy group using the DCC/DMAP method resulted in unacceptable yields of C4 acyl derivatives, but the use of acid chloride and LiHMDS in THF at 0° C. gave the desired C-4 modified baccatin derivatives (9a, c-e), with yields ranging from 52-78%. However, in FIG. 5, 8 with 3-butenoyl chloride did not give any required product 9b. A minor product acylated at the C-4 position, but with a loss of the 1-dimethylsilyl group, was always obtained in this step, and it was used for the subsequent step. Global deprotection of (9a, c-e) using HF.pyridine, followed by a selective C-10 acetylation (see, Holton et al., *Tetrahedron Lett.* 39:2883-2886 (1998)) with 0.1 mol % of CeCl$_3$ and acetic anhydride in tetrahydrofuran, gave a more than 90% yield of the desired 10-acetyl derivatives (10a-d). The selective protection of the C7 hydroxyl as the triethylsilyl ether afforded 11a-d in good yields.

The reagents and conditions used in Scheme 3, as presented in FIG. 5, were: a. LHMDS, THF 0° C., acroylyl chloride ((9a, 52% yield), 3-butenyoyl chloride (9b, 0%), 4-pentenoyl chloride (9c, 78% yield), 5-hexeneoyl chloride (9d, 71% yield), 6-heptenoyl chloride (9e, 40% yield); b. (i) HF.Py, THF (n=0, 60%, n=2, 91%, n=3, 80%, n=4, 44%), (ii) CeCl$_3$, Ac$_2$O, THF (10a, (n=0) 89%), (10b, (n=2) 92%), (10c, (n=3) 89%), (10d, (n=4) 95%); c. triethylsilyl chloride, imidazole, DMF (11a, n=0, 87%), (11b, n=2 85%), (11c, n=3 72%), (11d, n=4 83%).

Figure 6:
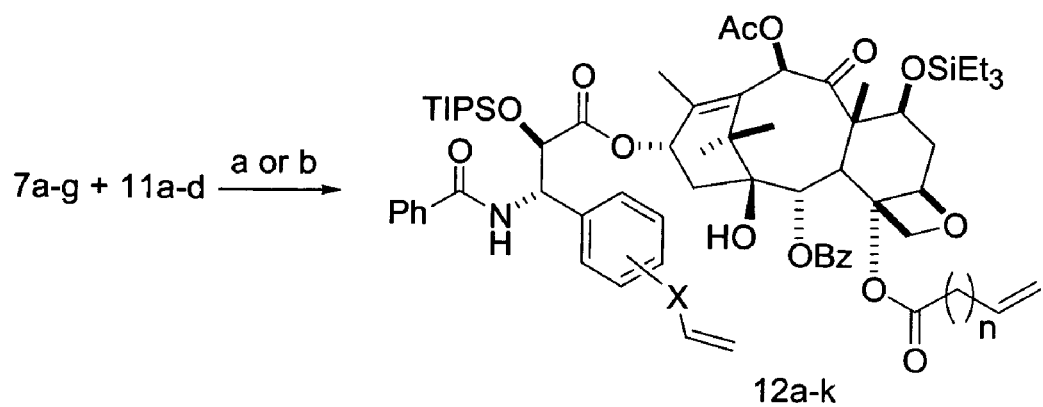
FIG. 6 illustrates synthetic scheme 4.

Having made several baccatin III derivatives (11a-d in FIG. 5) and β-lactam derivatives (7a-f), ω,ω'-diene taxoid precursors 12a-k (see, FIG. 7) where synthesized according to Scheme 4 presented in FIG. 6 with yields ranging from 50-92% using Holton-Ojima-Georg protocols (see, Holton et al., *Taxol: Science and Application* CRC Press: New York, 1995, pp. 97-121; Georg et al, *Taxol: Science and Application* CRC Press: New York, 1995, pp. 317-375; and Ojima et al., *J. Org. Chem.* 63:1637-1645 (1998)). These dienes then were used in the ring closing metathesis reaction. The reagents and conditions used in Scheme 4 were: a. LHMDS THF, –40° C.; b. NaH, THF, 0° C.-RT.

The reagents and conditions used for the synthesis of taxoid ω,ω' dienes presented in tabular form in FIG. 7 were as follows: Baccatin III derivative (1 eq) in THF was treated with LiHDMS (1.4 eq) at –40° C. for 3-4 h., or Baccatin III derivative (1 eq) in THF was treated with NaH (excess) at 0° C. for 15 min and then treated with β-lactam (2 eq) 0° C. and brought to room temperature over 12h. 13a-j (see FIG. 8) were synthesized by deprotection of 12 a-j with HF.Py in THF at 0° C.-room temperature over 12h.

The ω,ω'-diene substrates 12g, 12h were synthesized to explore macro-cyclization using the ring closing metathesis reaction with Grubbs's first generation catalyst in dichlormethane at high dilution conditions. These have resulted in exclusively Z-olefinic macrocyclic analogs 14e and 14f. (see FIG. 8 where the synthesis of macrocyclic PTX analogs are presented in tabular form). The second generation Grubbs's catalyst at the same high dilution condition in dichloromethane proved highly efficacious for other substrates (12c, 12d) yielding exclusively E (14a, 14b and 14c), and E/Z separable mixtures for other ω,ω' dienes.

The reagents and conditions for the PTX analogs (derivatives) presented in FIG. 8 are as follows: a. ω,ω' dienes in CH$_2$Cl$_2$ was treated with Grubbs's second generation catalyst in CH$_2$Cl$_2$ for 2-3 h at room temperature. b. deprotection of 14a-j with HF.Py in THF at 0° C.-room temperature provided 15a-j c. hydrogenation of 15a-j with 10% Pd-C at 35 psi and room temperature in methanol provided 16a-h and 16j.

Figure 10:
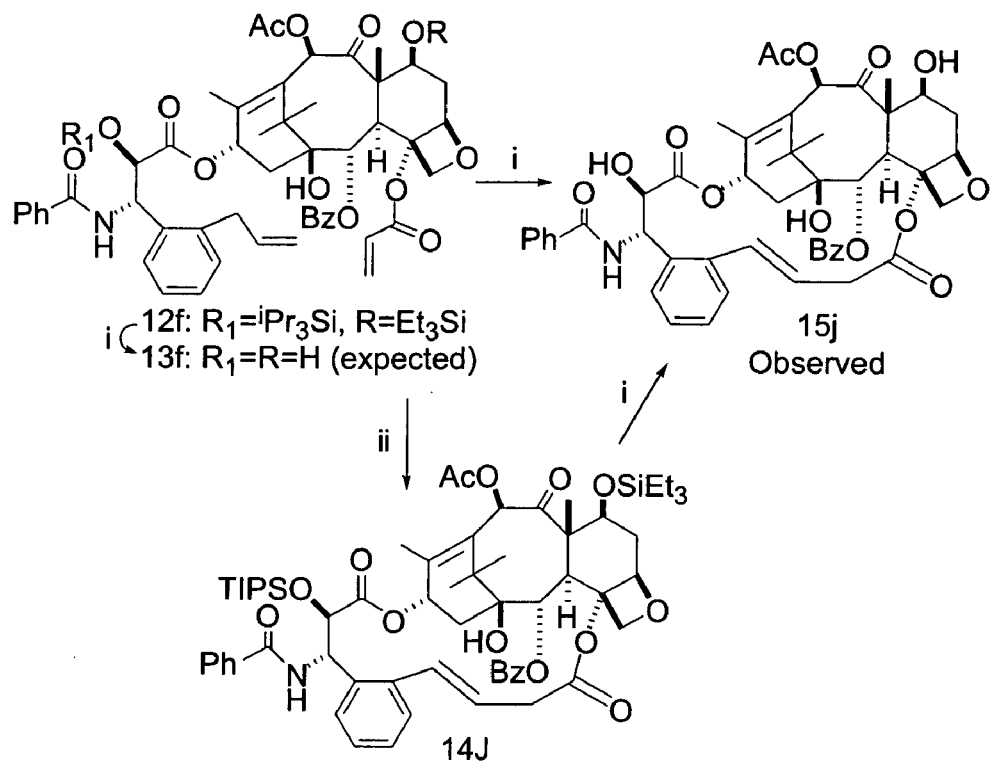
FIG. 10 illustrates synthetic scheme 5.

A biological evaluation of macrocyclic bridge PTX analogs or "derivatives" of the present invention was conducted. As pointed out above, any of the proposed bioactive models should be supplemented with a conformationally constrained analog that mimics this model in solution and should possess an equal or greater bioactivity with respect to parent compound. To achieve such a conformationally constrained analog that would support the bioactive conformation of PTX, 21- and 19-membered macrocyclic analogs (15e, 15f) with 8 and 6 atoms, respectively, in the bridge between C-4 acetyl and the C-3'-phenyl m-position of PTX, were synthesized. These analogs exhibited comparable cytotoxicity (with about 10-30 fold less) against A2780 (an ovarian cancer cell line) and tubulin polymerization (TP) activity compared to PTX. In an effort to understand the reduced activities of 15e, the conformational profile of compound 15e in solution was sought out by means of an NMR analysis of molecular flexibility in solution (NAMFIS) conformer deconvolution treatment. The best fit T-form of compound 15e is seated higher in the taxol binding pocket as a result of close contact between the propene moiety of the tether and Phe272 of the protein at the bottom of the illustration. The dihydroderivatives 16e and 16f were also synthesized by hydrogenation of 15e and 15f, respectively, to evaluate as alkane bridge macrocyclic taxoids. However, the bioactivity of fully saturated bridge compounds was much less than the unsaturated 15e and 15f. Surprisingly, the open analogs 13h and 13i showed better cytotoxicites than their macrocyclic counter parts 15e and 15f. (see particularly the tabular results presented in FIG. 10).

Once conversant with the interaction of C-3' meta bridged macrocyclic taxoids 15e and 15f with tubulin, bridged compounds were made with the tether connecting from the ortho position of C-3'-phenyl, rather than the meta position to C4 position of PTX. Eventually, with the similar ring closing metathesis strategy, the 20 to 22 membered macrocyclic taxoids 15g-i and their dihydroderivatives 16g-h with 8-10 atoms in the bridge, respectively, were synthesized. The biological potential of 15g-i and their dihydro analogs 16g-h were comparable to PTX (with about 10-30 fold less activity). Interestingly, the open chain analogs 13i-k (of 15g-i) were found to be inactive against the A2780 cancer cell line (see the tabular results in FIG. 10).

Shorter bridge compounds were made by reducing the tether length. Two macrocyclic taxoids, 15b and 15c, and their saturated dihydroderivatives, 16b and 16c, with 6 or 7 atoms in the bridge between C4 and the C-3' phenyl ortho position of PTX were synthesized. These 18-membered macrocyclic taxoids, 15b-c and 16b-c, exhibited remarkably more or less equal cytotoxicity against A2780 and PC3 (prostate cancer) cell lines, except for the compound 15b, which showed two fold more cytotoxicity than PTX against the PC3 cell line. Comprehensive conformational NMR/NAMFIS study and docking the NMR/NAMFIS derived conformation of 15b into the tubulin binding pocket showed us the best fit T-form (of 15b). It not only seats itself into the tubulin binding pocket, escaping the steric clash15 (as we observed for meta bridge compounds 15e16), but it also nicely accommodates the His 227 of β-tubulin by constraining the molecule to bioactive conformation by bridging behind the stacked rings. Intrigued by the bioactivity profile of the 15b, the bridge has been further refined and truncated, and consequently 17-membered macrocyclic taxoid 15d and its saturated dihydroderivative 16d, with 7 atoms in the bridge and without the oxygen atom, has been synthesized. Gratifyingly, the bridged taxoid 15d exhibited excellent bioactivity at least 20 times more potent than PTX against A2780, and 16d showed about 10 times more activity than PTX against the A2780 cell line. These two taxoids also showed slightly more cytotoxicity than PTX against the PC3 cell line.

To verify the unusual activity of 15b, 15d and 16d, the biological evaluation of the open chain analog 13c (of 15b) was investigated, and it was found to be almost inactive against both the cell lines mentioned above. This demonstrates that the activity associated with the cyclic taxoids originated from conformational restriction, and not from structural modifications at C4 and the ortho position of C-3' phenyl group.

Efforts to synthesize 13f (as an open analog of 15d) from 12f under HF-pyridine deprotection conditions yielded a surprising outcome, and it resulted in a cyclic derivative (15J) with an unprecedented transformation (see Scheme-5 in FIG. 9). 15J was also obtained from an alternate route via 14J. 12f was in CDCl$_3$ for 5 days and produced the cyclic taxoids 14J following a similar (but not yet known) unprecedented transformation (elimination of a 2-carbon olefin unit from C4-acryloyl group), which was then subjected to HF pyridine to generate 15J in satisfactory yield. At this point, the precise mechanism for the conversion of 15J from 12f (rather than 13f) in the presence of HF.pyridine, and the similar conversion of 14 from 12f, was unknown. However, the structure of 14J and 15J was well-established using complementary 2D NMR spectroscopic data. Further, the bioactivity results of 15J (7 atom trans olefinic bridge) is promising, and this compound exhibited remarkably 6-fold more cytotoxicity compared to PTX against the A2780 cell line and 2-fold more against the PC3 cell line.

Figure 11:
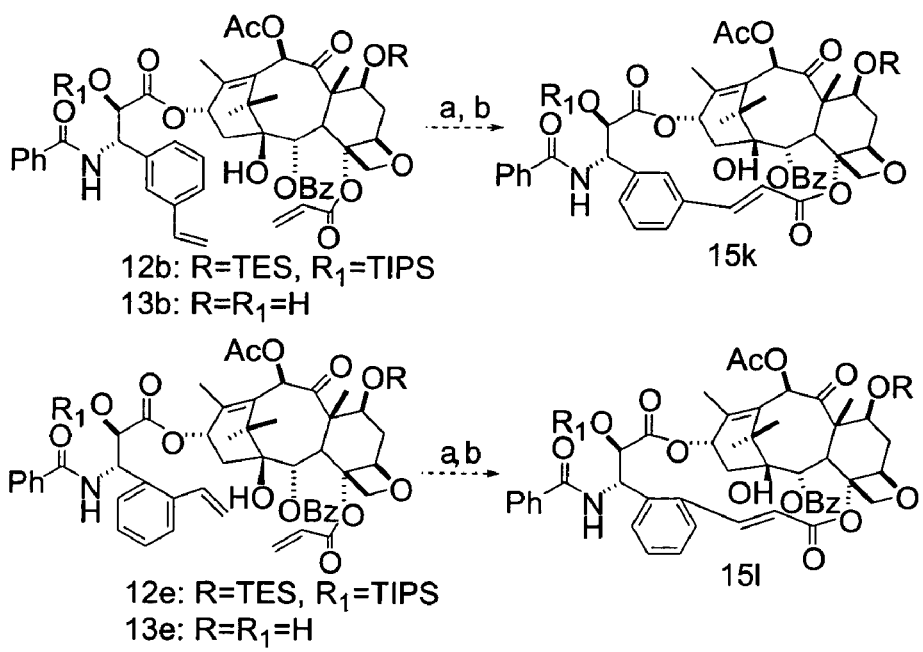
FIG. 11 illustrates synthetic scheme 6.

Efforts to make still smaller ring macrocyclic taxoids (namely 15k and 15l), with respect to 15b, from the dienes 12b and 12e were unsuccessful. The dienes 12b and 12e and/or their deprotected dienes, 13b and 13e, did not undergo ring closing metathesis using either Grubbs catalyst under various solvents and temperature conditions to generate 15k and 15l (Scheme 6 in FIG. 11).

The tubulin polymerization activity of 15b, 16b and 15J were superior to PTX (see the tabular information in FIG. 10), and all these taxoids were able to inhibit the binding of fluorescent taxol better than paclitaxel. In the tubulin polymerization assay, competition experiments with fluorescent taxol and 15b was found to be identical in all respect to PTX.

The extensive conformational and modeling studies on the most active bridged taxoids (15b-d) proved that these taxoids adopt the T-conformation in solution, and that this conformation was docked in the tubulin binding pocket.

An important and intriguing factor is that some of the bridged taxol analogs displayed promising bioactivity against paclitaxel resistant and epothilone A resistant cell lines, as shown in Table 4 of FIG. 9. More specially the bridged taxoid 15d and its dihydro analogs 16d have exhibited 100 times better activity than paclitaxel, and the few other bridge taxoids were equally and/or little better than paclitaxel.

As discussed above, and in the Examples below, a wide variety of paclitaxel (PTX) analogs or "derivatives" have been synthesized, and these derivatives are representative of a new family of constrained paclitaxel derivatives which include a ridge from the C-3' phenyl group to the C-4 position, or a bridge from the C-3' phenyl group to the C-3 position in the case where the C-4, C-5, C-6, and C-7 carbons have been eliminated. The bioactivity information which has been generated suggests that many of these paclitaxel derivatives will be suitable as substitutes for paclitaxel in the treatment of human cancers such as ovarian cancer, breast cancer and lung cancer, as well as neurodegenerative diseases such as Alzheimer's. The paclitaxel derivatives would be administered to a patient in need thereof by the medhanism used for the current natural product paclitaxel (Taxol™). The paclitaxel derivatives of this invention may preferably be provided in combination with an emulsifying agent and an alcohol. Elixirs, antimicrobials (parabens, benzylalkonium chloride, etc.), and other constituents can be combined with the paclitaxel derivatives of the present invention. These paclitaxel derivatives may be administered via a variety of pathways including intravenous, interperitoneal, oral, sublingual, inhalation, and other suitable methodologies as appropriate. These paclitaxel derivatives will also be useful in screening for the performance of similar bridged paclitaxel derivatives within the family described by this invention.

Examples of the types of paclitaxel derivatives with constrained conformations that are encompassed by the present invention include:

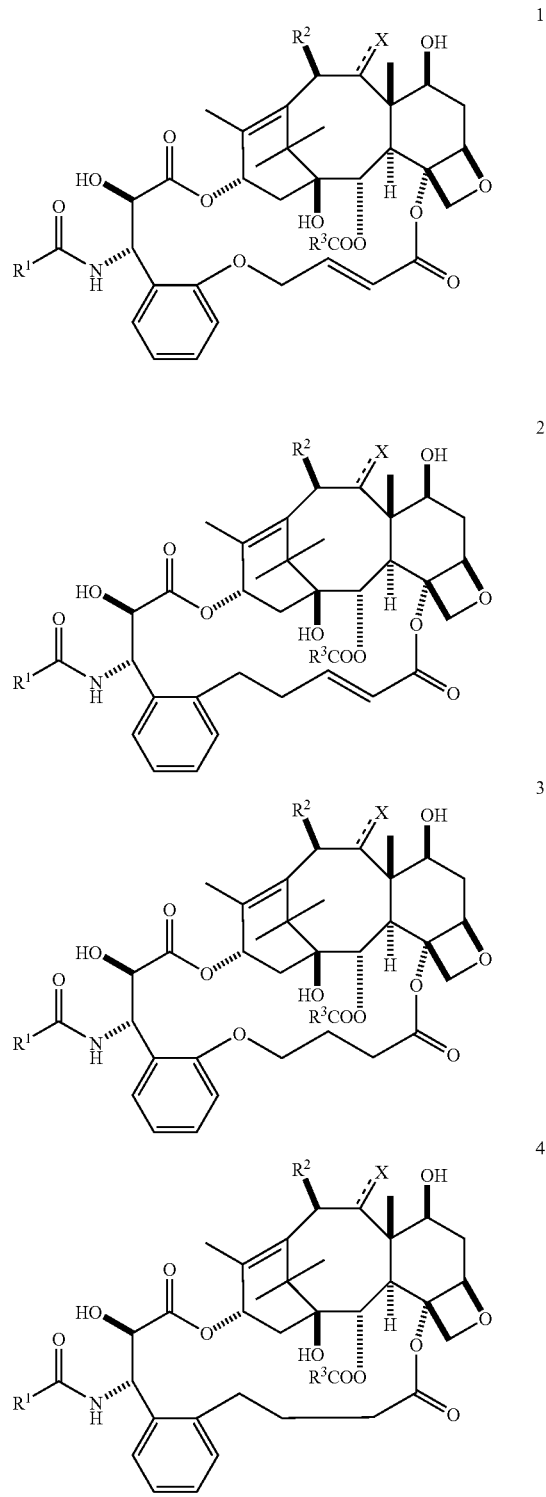

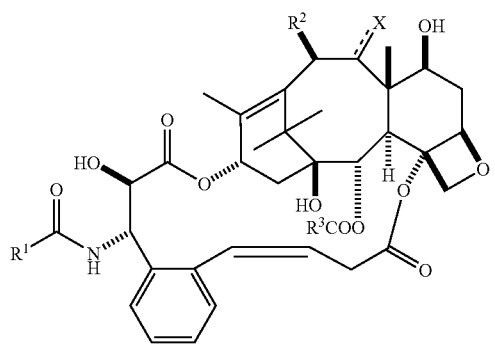
5
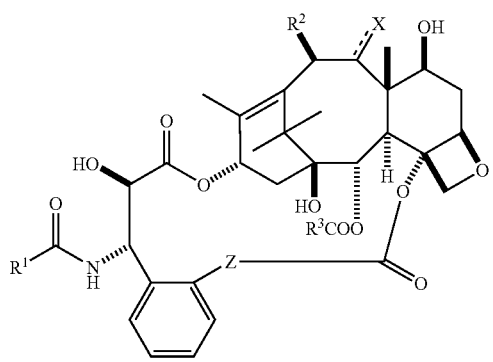
9
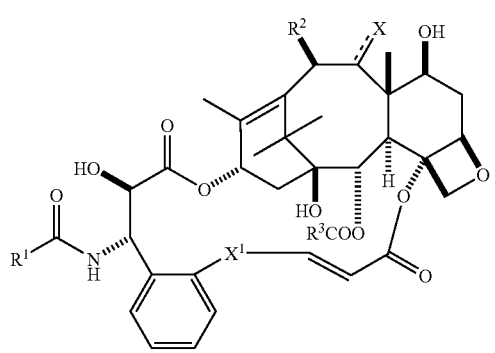
6
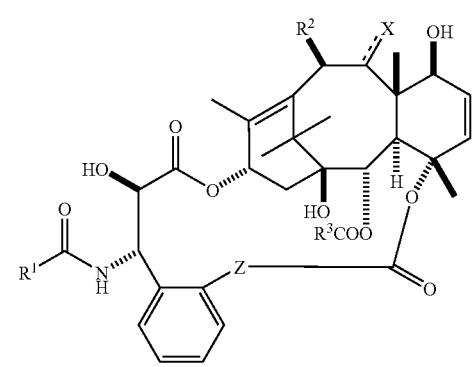
10
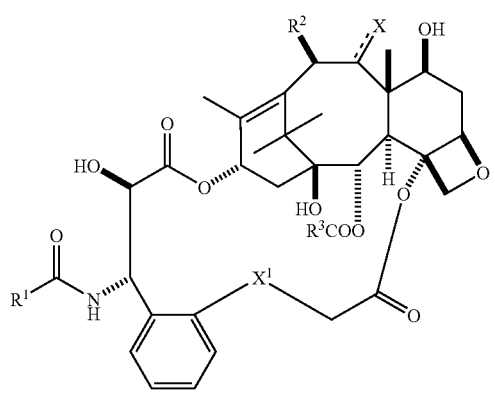
7
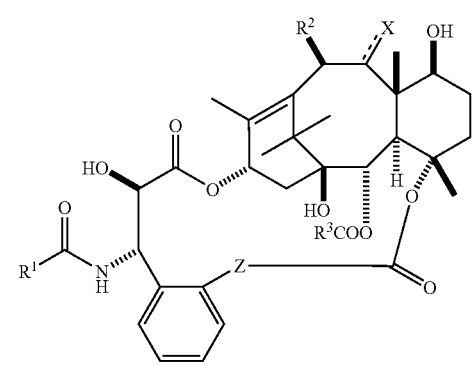
11
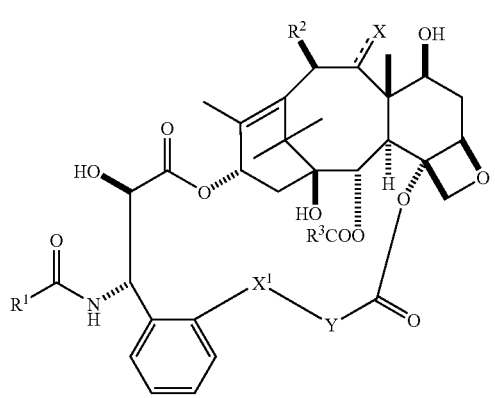
8
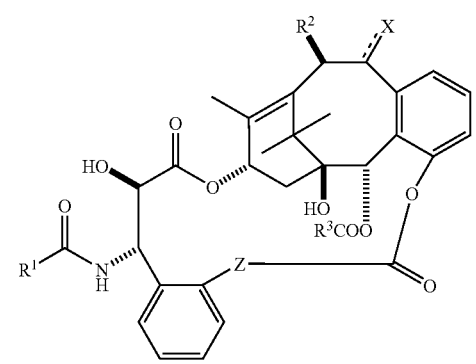
12

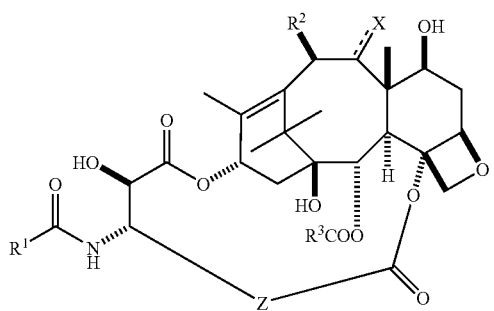
13
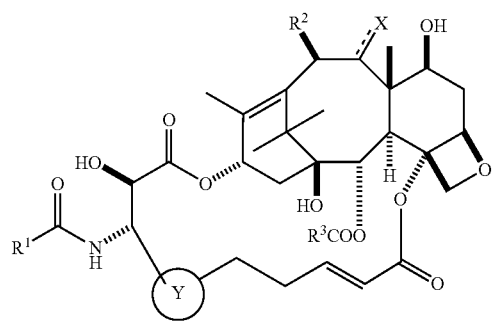
18
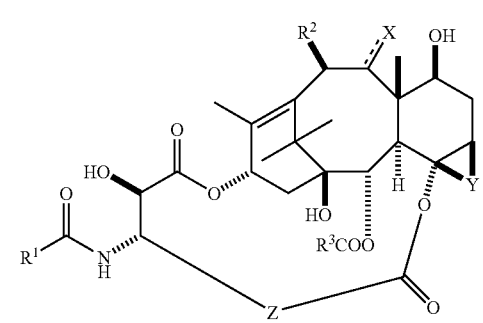
14
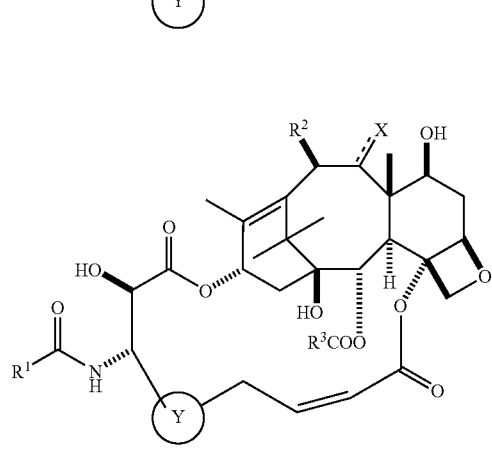
19
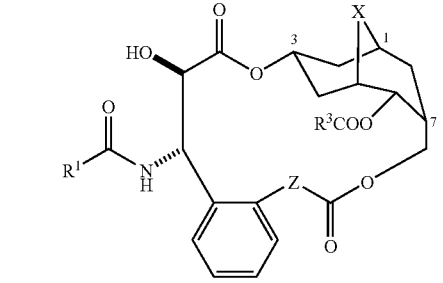
15
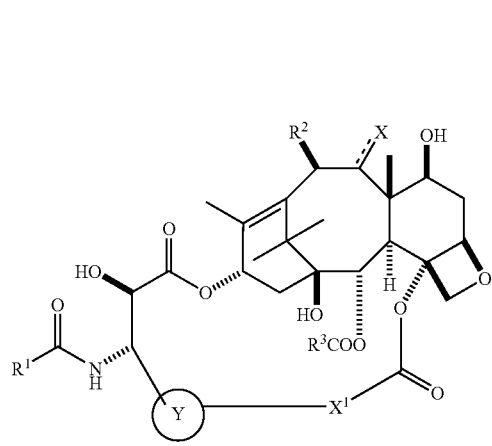
20
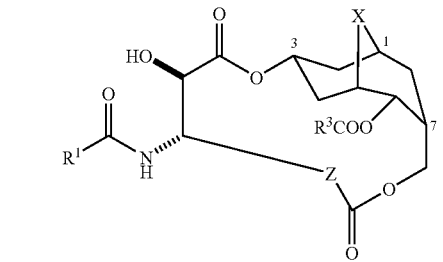
16
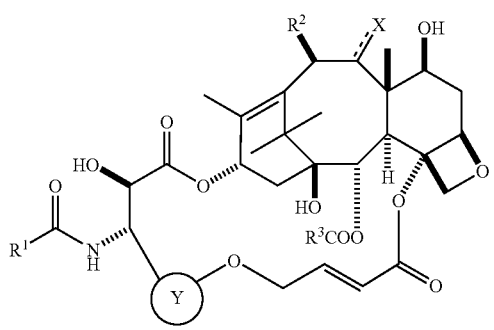
17
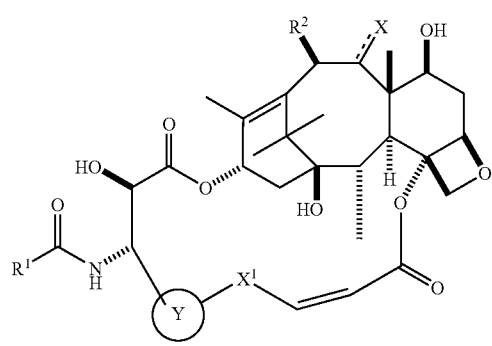
21

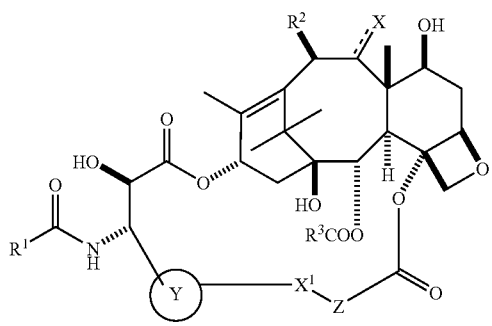

22

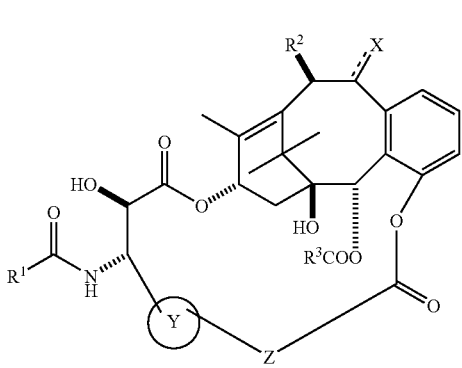

26

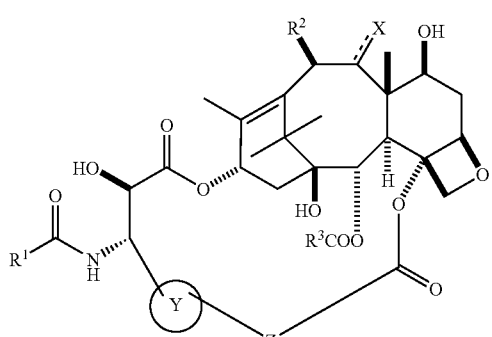

23

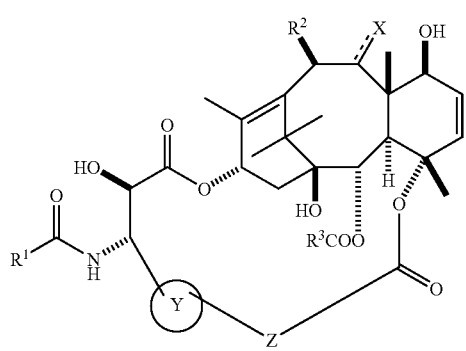

24

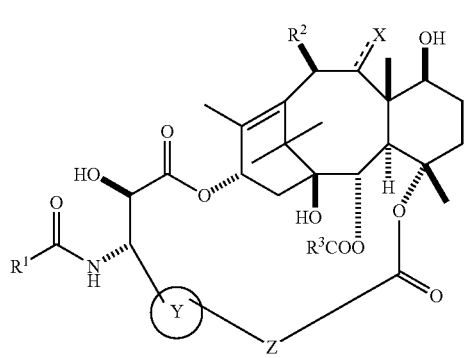

25

In these structures, X may be O, $CH_2$, S, NH, OH and $NH_2$; $R^1$ may be $C_1$ to $C_{10}$ linear or branched chain alkyl, alkenyl, and alkoxy groups, and substituted and unsubstituted aryl and heteroaryl rings, with phenyl and $(CH_3)_3CO$ being the preferred embodiments; $R^2$ may be hydrogen, OH, and $OCOR^4$, where $R^4$ is a $C_1$ to $C_{10}$ linear or branched chain alkyl, alkenyl, or alkoxy group; $R^3$ may be methyl, a $C_1$ to $C_{10}$ linear or branched chain alkyl or alkenyl group, and an aryl or heteroaryl group, with phenyl, o-methoxypheny, 1,4-dimethoxyphenyl, m-methoxyphenyl, m-chlorophenyl, m-azidophenyl, m-fluorophenyl, 2,4-difluorophenyl, m-aminophenyl, or m-bromophenyl being the preferred embodiments. $X^1$ may be $OCH_2$, $SCH_2$, OCO, $OCOCH_2$, $OCH_2CH_2$, $OCH_2CH_2CH_2$, $CH_2CH_2$, $CH_2OCH_2$, $CH_2SCH_2$, $CH_2CH_2CH_2$, $SCH_2CH_2CH_2$, $SCH_2CH_2$, $CH_2OCH_2CH_2$, $CH_2SCH_2CH_2$, $CH_2CH_2CH_2CH_2$, and the $CH_2$ units can be replaced by CHM where M=alkyl, OH, $OCH_3$, $NH_2$, F, Cl, Br, I, $CO_2H$ or $CO_2R$ (where R=alkyl); and the $CH_2$ units can be replaced by CHM where M=alkyl, OH, $OCH_3$, $NH_2$, F, Cl, Br, I, $CO_2H$ or $CO_2R$ (where R=alkyl), and the double bond in the bridging chain can be either cis or trans; Y may be O, S, and NH; and Z is any chain of one to six atoms or groups drawn from the individual units of O, S, $SO_n$ (n=1,2), $CH_2$, CHR(R=alkyl), NH, C=O, $CR_1=CR_2$($R_1$=H, alkyl, $R_2$=H, alkyl) or C≡C.

EXAMPLES

Example 1

The Bioactive Taxol Conformation on β-Tubulin: Experimental Evidence from Highly Active Constrained Analogs The diterpenoid natural product Taxol (1a) and its semi-synthetic analog docetaxel (1b) are clinically important antitumor agents whose clinical uses are still being expanded as various combination therapies are being explored. They are known to exert their therapeutic effect, at least in part, by their ability to promote the assembly of tubulin into microtubules. In recent years, several other natural products have been discovered which have a similar mechanism of action to Taxol, including discodermolide (2), epothilone B (3), and eleutherobin (4). These compounds, together with several new analogs of Taxol, are all in preclinical development or in clinical trials as potential new antitumor agents.

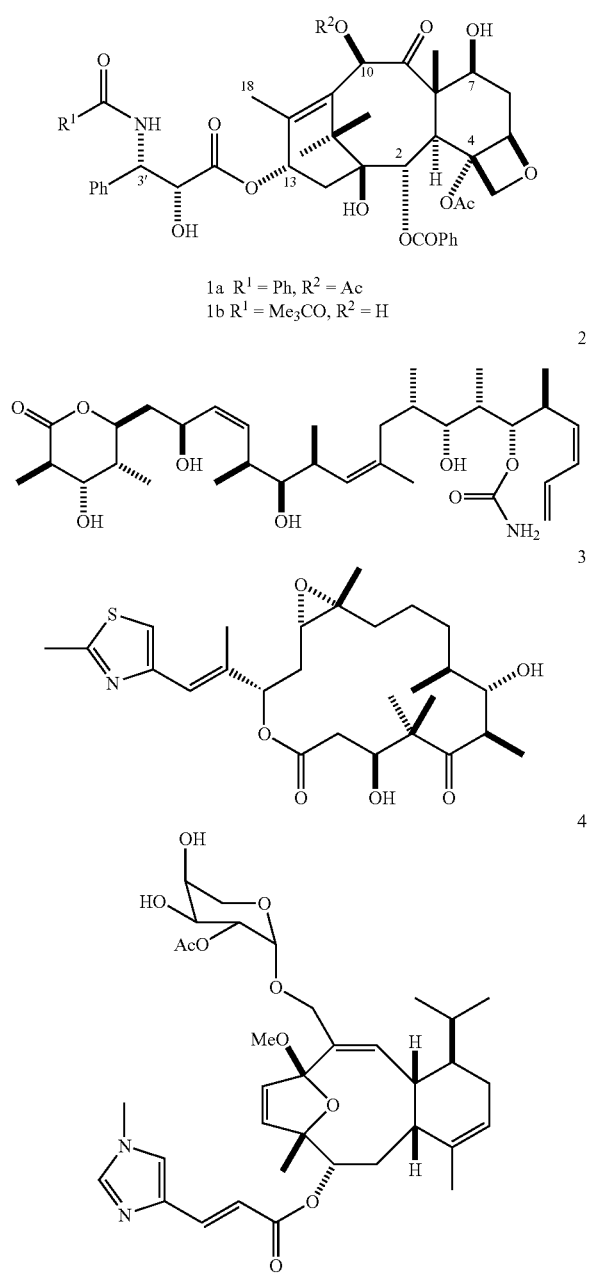

1a $R^1$ = Ph, $R^2$ = Ac
1b $R^1$ = Me$_3$CO, $R^2$ = H

2

3

4

Taxol has been shown to bind to assembled microtubules and to stabilize them. It binds with an approximate stoichiometry of 1 mole of Taxol to 1 mole of tubulin dimer, stabilizes the polymer and disrupts the equilibrium between tubulin and microtubules, leading to cell death by apoptosis. Taxol also binds to Bcl-2, which then undergoes hyperphosphorylation, but it has been shown that this effect is linked to Taxol's tubulin-assembly activities. It has been proposed that Taxol-promoted microtubule assembly leads to Raf-1 activation and Bcl-2 phosphorylation, and thence to apoptosis. The tubulin-binding activity of Taxol (and, by implication, of other compounds that have similar effects) thus appears to be the key to its antitumor activity.

The interaction of Taxol with tubulin has been studied intensively by several methods. Thus, photoaffinity labeling has shown that a 3'-(p-azidobenzamido)Taxol derivative labels the N-terminal 31 amino acids of p-tubulin, while 2-(m-azidobenzoyl)Taxol labels residues 217-231 of β-tubulin, and a C-7 benzophenone derivative labeled Arg$^{282}$ in β-tubulin. Fluorescence spectroscopy has yielded valuable information, but the most important results to date have come from the recently determined 3.7 Å structure of the αβ-tubulin-Taxol complex obtained by electron crystallography of zinc-induced tubulin sheets. Although this structure shows the location of the binding site on β-tubulin, it does not enable the conformation of the ligand to be determined.

Knowledge of the conformation of Taxol in its bound state on the microtubule has important ramifications. On one hand, it offers one piece of the puzzle that presently obscures the basis for the similar biological activity of the four very different chemical compounds 1-4. On the other hand it can provide a conceptual model for the synthesis of simplified analogs that may well retain the full activity of the parent compound. Several experimental attempts to identify this conformation have been made by NMR measurement of internuclear distances within Taxol bound to microtubules, and by the synthesis of various conformationally restricted Taxol analogs. In addition, studies have compared the conformations of Taxol and epothilone B by molecular modeling and other methods. Separate investigations have proposed distinguishable conformations of the Taxol side chain, with a T-shaped conformation being favored on the basis of its fit with the election-density map of zinc-induced tubulin sheets. In the present work we provide experimental evidence that Taxol can be constrained to the T-conformation in solution, and that this form both stabilizes genuine microtubules and induces cell death.

Materials and Methods

Figure 12:
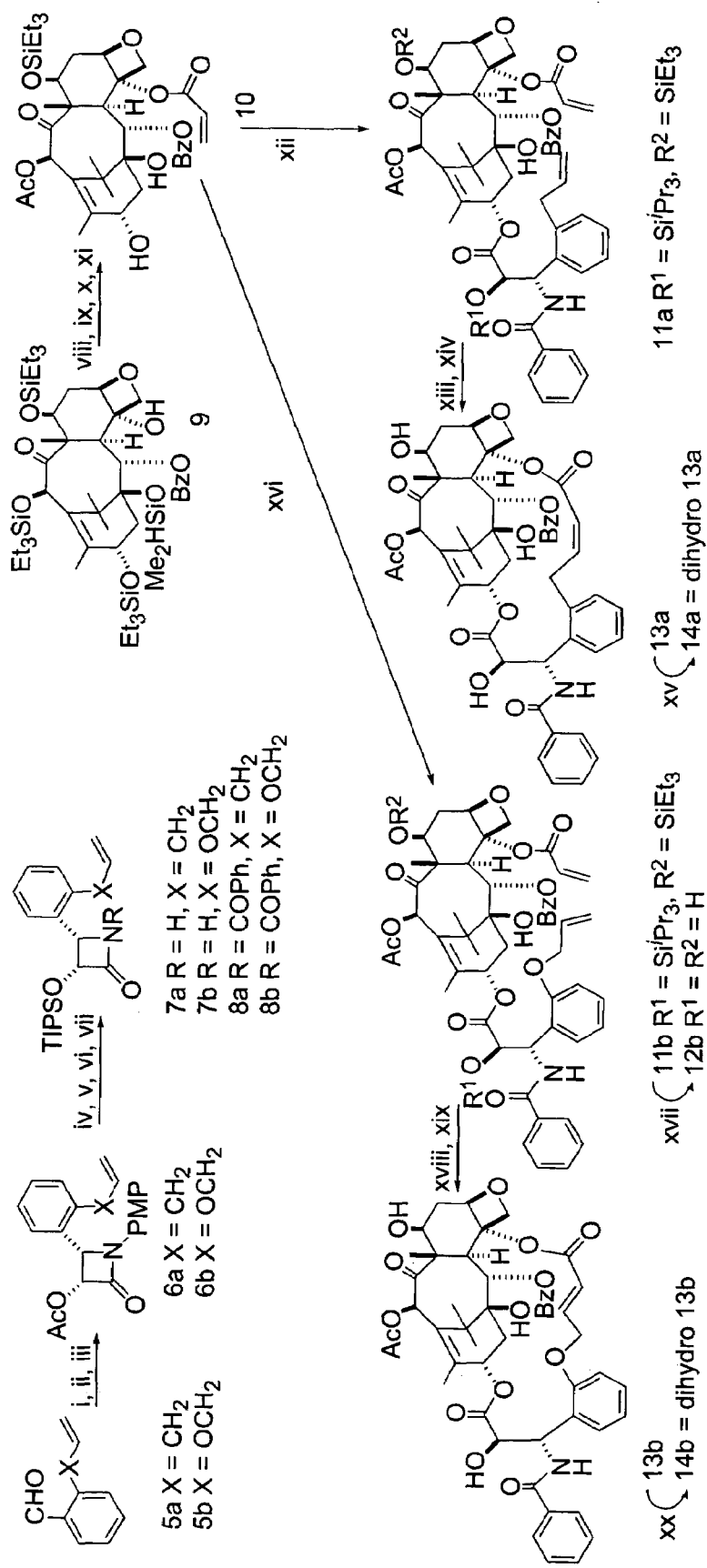
FIG. 12. Synthetic scheme for the bridged paclitaxels 13a, 13b, 14a, and 14b. The reagents and conditions for the "a" series of β-lactams were similar to those below for the "b" series. Reagents and conditions for the "b" series β-lactams: i, 5b, p=MeOC$_6$H$_4$NH$_2$, MgSO$_4$, CH$_2$Cl$_2$, 100%. ii, CH$_3$COOCH$_2$COCl, Et$_3$N, −78° C. to rt, 12 h, 85%. iii. Lipase (Amano PS), phosphate buffer, pH 7.2, CH$_3$CN, 24 h, 98%. iv. 1M KOH, THF, 0° C., 100%. v. TIPSCl, imidazole, DMF, 94%. vi. CAN, CH$_3$CN, −5° C., 62%. vii. PhCOCl, Et$_3$N, DMAP, CH$_2$Cl$_2$, 95%. viii. LiHMDS, THF, 0° C., CH$_2$=CHCOCl, 52%. ix. HF-pyridine, THF, 70%. X. CeCl$_3$, Ac$_2$O, THF, 96%. Xi. Et$_3$SiCl, Imidazole, DCM, 72%. xii. 8a, NaH, THF, 0° C.-rt, 24h. xiii. ((Cy$_3$)P)(H$_2$IMes)Cl$_2$Ru=CHPh, CH$_2$Cl$_2$, 3 h, xiv. HF-pyridine, 12 h. xv. H$_2$, Pd/C(10%), 35 psi, 2.5h. xvi. 8b. NaH, THF, 0° C.-rt, 24h, 50%. xvii. HF.Pyridine, THF, 81%, xviii. ((Cy$_3$)P)(H$_2$IMes)Cl$_2$Ru=CHPh,CH$_2$Cl$_2$, 3h,64%. xix. HF-pyridine, 12h, 98%. xx, H$_2$, Pd/C(10%), 35 psi, 2.5h, 96%.

Synthesis of Open Chain Analogs 12b and Bridged Analogs 13a, 13b, 14a, and 14b. FIG. 12 outlines the synthesis of bridged Taxol derivatives 13a, 13b, 14a, and 14b, together with the open-chain analog 12b. Experimental details and characterization data for the intermediates are presented below under Compound Synthesis.

Critical Concentration Determination. The critical concentration of tubulin in the presence of 10 μM Taxol or Taxol analog was determined from assembly experiments performed at 37° C. with GDP-tubulin in PME buffer (100 mM PIPES, 2 mM MgSO$_4$, 1 mM EGTA, pH=6.90) containing 4% DMSO. The extent of assembly was measured at different tubulin concentrations (0.5-6 μM) by light scattering (apparent absorption at 350 nm). Critical concentrations were calculated from the x-intercepts of plots of apparent $A_{350\,nm}$ VS. tubulin concentration.

Competition Binding Experiments. The relative affinities of Taxol and derivatives for polymerized tubulin were assessed by competition assays. Crosslinked microtubules were prepared in glycerol assembly buffer (10 mM phosphate, 1 mM EGTA, 0.1 mM GTP 3.4 M glycerol, pH 6.9) as described by Andreu and Barasoain. Prior to use, the crosslinked microtubules were dialyzed against PME buffer for 16-18 hr. Crosslinked microtubules (5 μM) and the fluorescent Taxol derivative N-AB-PT (15, 5 μM) in PME buffer were incubated for 20 min at room temperature with 10 μM of Taxol or the Taxoid. The fluorescence emission intensity at 412 nm of each sample was recorded using a Jobin-Yvon Horiba Fluoromax-3 spectrofluorometer in a 2 mm×10 mm quartz cell ($1_{ex}$=320 nm) and compared to the emission intensity of the system in the absence of competitor.

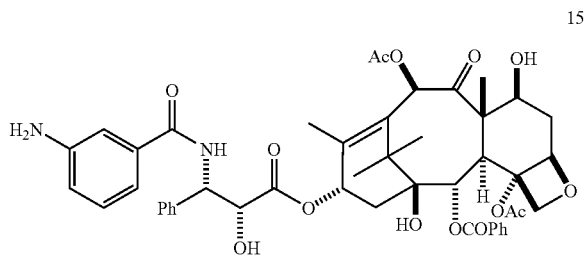

15

For the fall competition experiment, microtubules, N-AB-PT and varying concentrations of Taxol or 13b (0-30 μM) were treated in the same manner and their emission intensities were measured. The full competition experiment was repeated using pure tubulin assembled by N-AB-PT and identical results were obtained (data not shown).

Conformational Analysis for 13b in Solution. The 400 MHz ROESY analysis of 13b delivered 17 intramolecular distances. Monte Carlo conformational analysis using MacroModel 6.5 yielded 858 fully optimized conformations for 13b. Subsequent NMR/NAMFIS treatment integrated the latter and the ROESY spectra to yield three conformations in $CDCl_3$, two of which differ by torsions in the C-4 to C-3' bridge but correspond to a total of 83% of 13b in the T-Taxol form. For details, see the Supporting Information.

Results and Discussion

As summarized above, a series of studies point to a T-shaped Taxol conformer bound to β-tubulin in microtubules as being the best fit to the experimental data. However, definitive confirmation of this hypothesis is still lacking. As a result, experimental verification through independent but complementary methods was sought: molecular design, synthesis and tubulin binding studies of constrained T-Taxol analogs 13a, 13b, 14a, and 14b, and NMR analysis of conformation in solution.

Figure 13B:
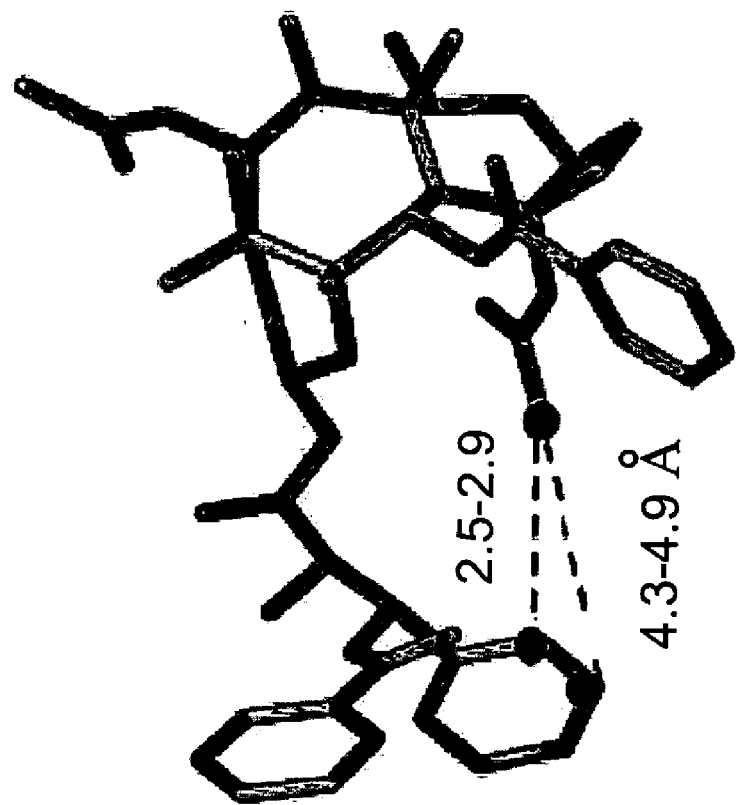
FIG. 13. T-Taxol conformation, a) The similar and extended ring to ring distances between the C-2 benzoyl phenyl and the C-3' phenyl and benzamido phenyl centers, respectively; b) H—H separations between the C-4 acetate methyl group and the ortho and meta positions of the C-3' phenyl ring.
Figure 13A:
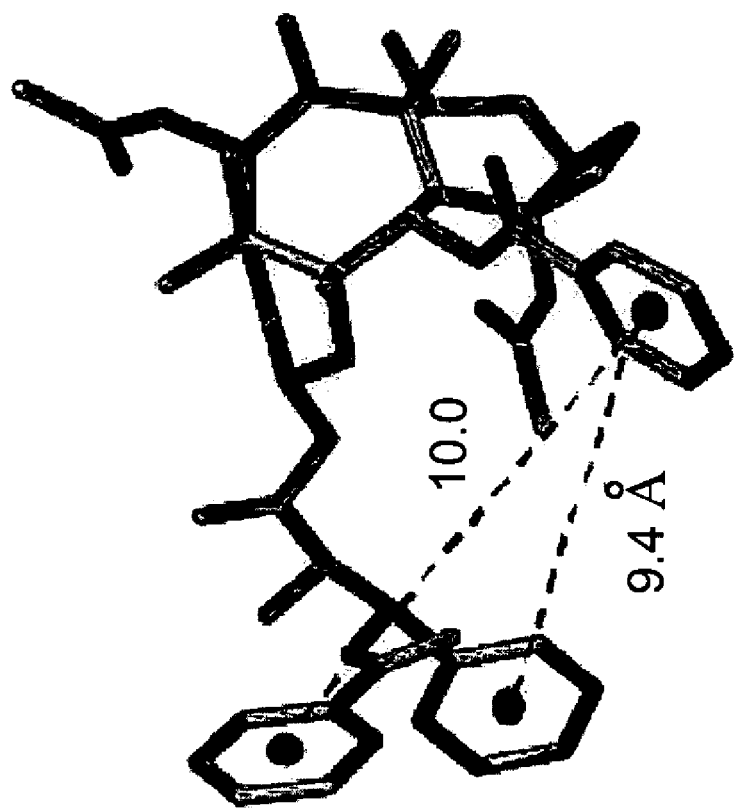

T-Taxol as a Design Template. The T-Taxol conformation, derived by docking experimentally based conformers of the ligand into the tubulin-Taxol electron crystallographic density shows several unusual features. Unlike a number of earlier propositions concerning the conformation of bound Taxol (e.g. reference 35) hydrophobic collapse between the C-2 benzoyl phenyl moiety and either of the phenyl rings emanating from C-3' is not observed. Rather, both of the latter rings reside 9-10 Å from the C-2 substituent (FIG. 13a). The overall spatial disposition of the C-13 side chain in the T-Taxol conformation resembles that of the so-called "non-polar" conformation in which the C-3' benzamidophenyl has been shifted significantly away from the C-2 benzoyl center. Examination of the computationally refined tubulin binding site illustrates that His227 resides between these two rings. This accounts for the fact that previous attempts to bridge the C-2 and C-3' positions has delivered either inactive Taxol analogs or compounds that are one or two orders of magnitude less active than Taxol itself. By contrast, inspection of T-Taxol reveals that the C-4 acetate methyl hydrogens are just 2.5-2.9 Å and 4.3-4.9 Å distant from the o- and m-positions of the C-3' phenyl, respectively (FIG. 13b), suggesting that a bridge between these centers would contribute to a reduction in conformational mobility while locking the structure into the T-conformer.

Consequently, a number of bridging units from the C-4 methyl to the C-3' phenyl that could be formed readily by ring-closing metathesis methodology were contemplated. Two initial proof-of-principle targets connected the meta position of the C-3' phenyl and the C-4 methyl with four-atom bridges, e.g. 16. The compounds proved to be 10-fold and 30-fold less potent than Taxol, respectively, as microtubule stabilizers and cytotoxins. Therefore, shorter ortho-bridged structures with three or four atoms separating the side-chains, namely 13a and 13b and their bridge-saturated analogs 14a and 14b were turned to. In an attempt to quantify the SAR of the modifications, the most recently parameterized 3D-QSAR Taxol minireceptor, Wang, M.; Lakdawala, A.; Snyder, J. P. unpublished.) was employed to evaluate the tubulin polymerization capacity of the structures. Both were predicted to show activity comparable to Taxol in complete accord with the subsequently measured biological quantities described below.

Bridged Taxol Synthesis. The ultimate test of the binding conformation of Taxol would be to prepare a conformationally constrained derivative that shows better activity than Taxol itself. Our earlier modeling studies on the bridged analog 16 revealed that the compound is seated higher than Taxol in the binding pocket of tubulin as a result of a close contact between the propene moiety of the m-phenol linked tether and Phe270 of the protein. Structural analysis forecast that a tether linked to the ortho position of the 3'-phenyl would be pulled closer to the baccatin core and thereby minimize the ligand-protein interaction. Thus, a number of bridged Taxols with linkages from the ortho position of the 3'-phenyl group to the C-4 acetyl methyl group were prepared. The synthesis of the key compounds 13a and 13b is shown in FIG. 12. The double bond in the bridging linker of 13a was shown to be Z based on the NMR coupling constant of the α-proton (J=11.5 Hz). No E isomer was detected in this case. Surprisingly the double bond in the bridging linker of 13b was found to be E (J=15.5 Hz). Hydrogenation provided the dihydro analogs 14a and 14b, while compound 12b was evaluated as an "open chain" analog of 13a and 13b to ensure that the αβ-unsaturated ester and 3'-phenyl substitutions alone were not responsible for any unusual activity.

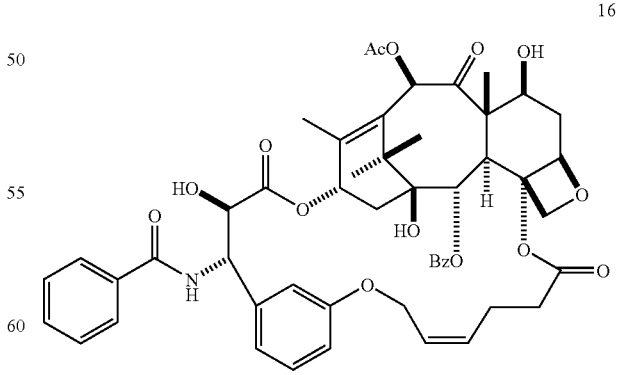

16

Microtuble Assembly and Cytotoxicity Assessment. Compound 13a proved to be highly active in two cytotoxicity assays (Table 1). In the A2780 ovarian cancer cell line it was approximately twenty times more potent than Taxol, and approximately 300-fold more potent than our previous best analog 15. In the PC-3 prostate cell line it was slightly more cytotoxic than Taxol. Compound 13b was equipotent with Taxol in the two cell lines. The dihydro compound 14a was more potent than Taxol in both cell lines, while the dihydro derivative 14b was slightly less potent when compared with the same standard. The "open chain" analog 12b was over three orders of magnitude less cytotoxic to A2780 cells and over two orders of magnitude less cytotoxic to PC-3 cells, demonstrating that the activity of 13a is not due to the presence of the αβ-unsaturated ester at C-4 or to the ortho substituent on the phenyl ring.

A characteristic in vitro activity of Taxol is its ability to induce purified tubulin to assemble into microtubules. The analogs' capability to promote tubulin assembly was roughly parallel to their cytotoxicities: compounds less cytotoxic than Taxol were also less potent promoters of assembly in these assays; conversely, compounds with cytotoxicities equal to or greater than Taxol were more effective polymerizing agents.

TABLE 1

Bioactivity of Taxol and Analogs 12-14.

| Compound | $IC_{50}(cp)/$ $IC_{50}(tx)$ A2780 | $IC_{50}(cp)/$ $IC_{50}(tx)$ PC3 | $ED_{50}$, Tb polymerization, $\mu M^c$ | Critical Tb conc., $\mu M^d$ | Inhibit binding F-Taxol, % |
|---|---|---|---|---|---|
| Taxol | a | b | 0.50 ± 0.14 | 1.8 ± 0.30 | 26 |
| 12b | 1190 | 150 | 1.02 ± 0.37 | ND | ND |
| 13a | 0.045 | 0.69 | 0.30 ± 0.09 | 0.53 ± 0.07 | 72 |
| 13b | 0.97 | 1.0 | 0.28 ± 0.11 | 1.2 ± 0.24 | 30 |
| 14a | 0.08 | 0.67 | 0.21 ± 0.09 | 0.35 ± 0.06 | 79 |
| 14b | 1.2 | 3.3 | 0.83 ± 0.19 | 1.3 ± 0.33 | 7 |

Figure 14:
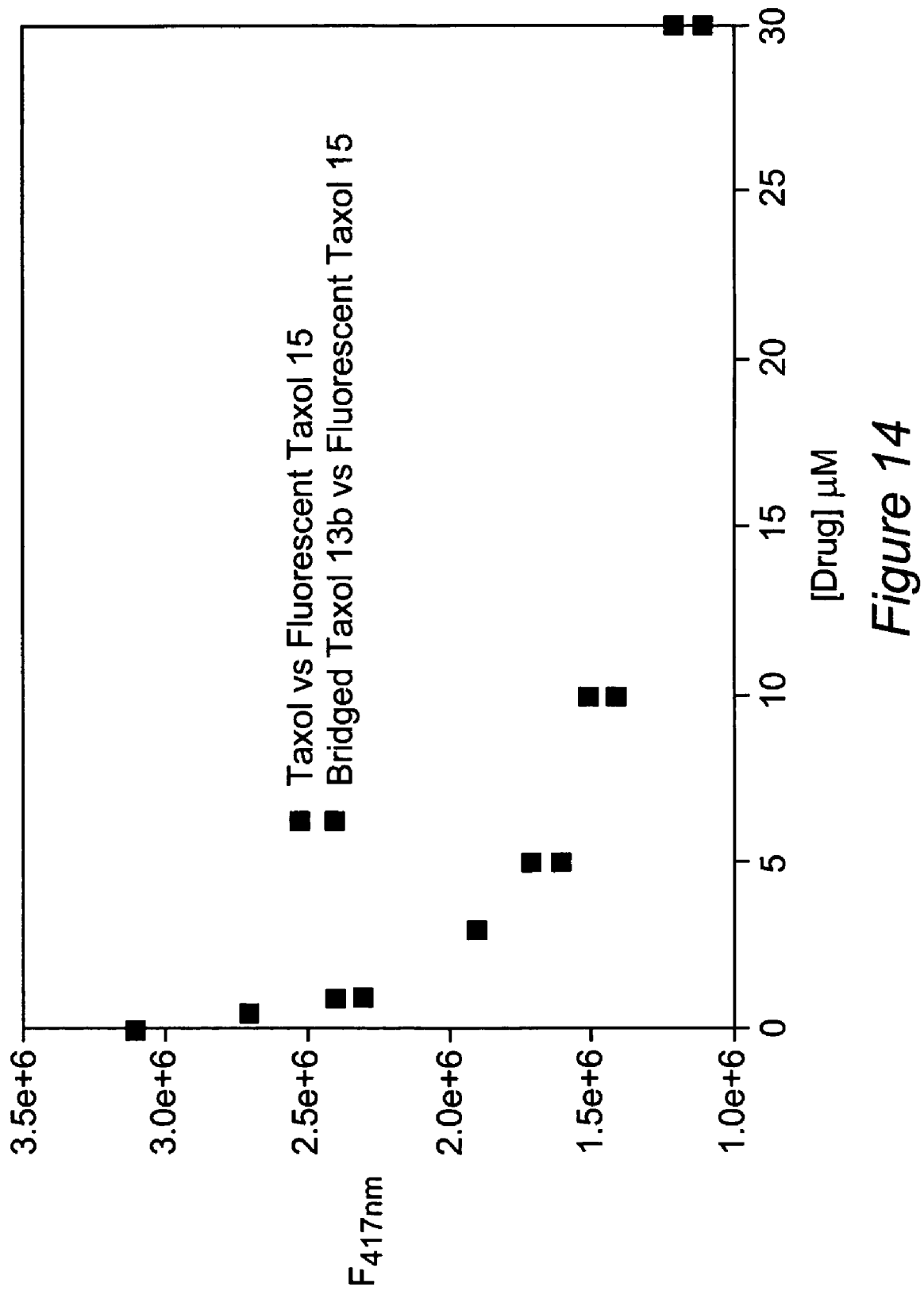
FIG. 14. Competition displacement of fluorescent Taxol 15 from tubulin by Taxol (black dots) and by compound 13b (black squares). Compound 15 was maintained at 5 μM, and increasing amounts of Taxol or compound 13b were added.
Figure 15:
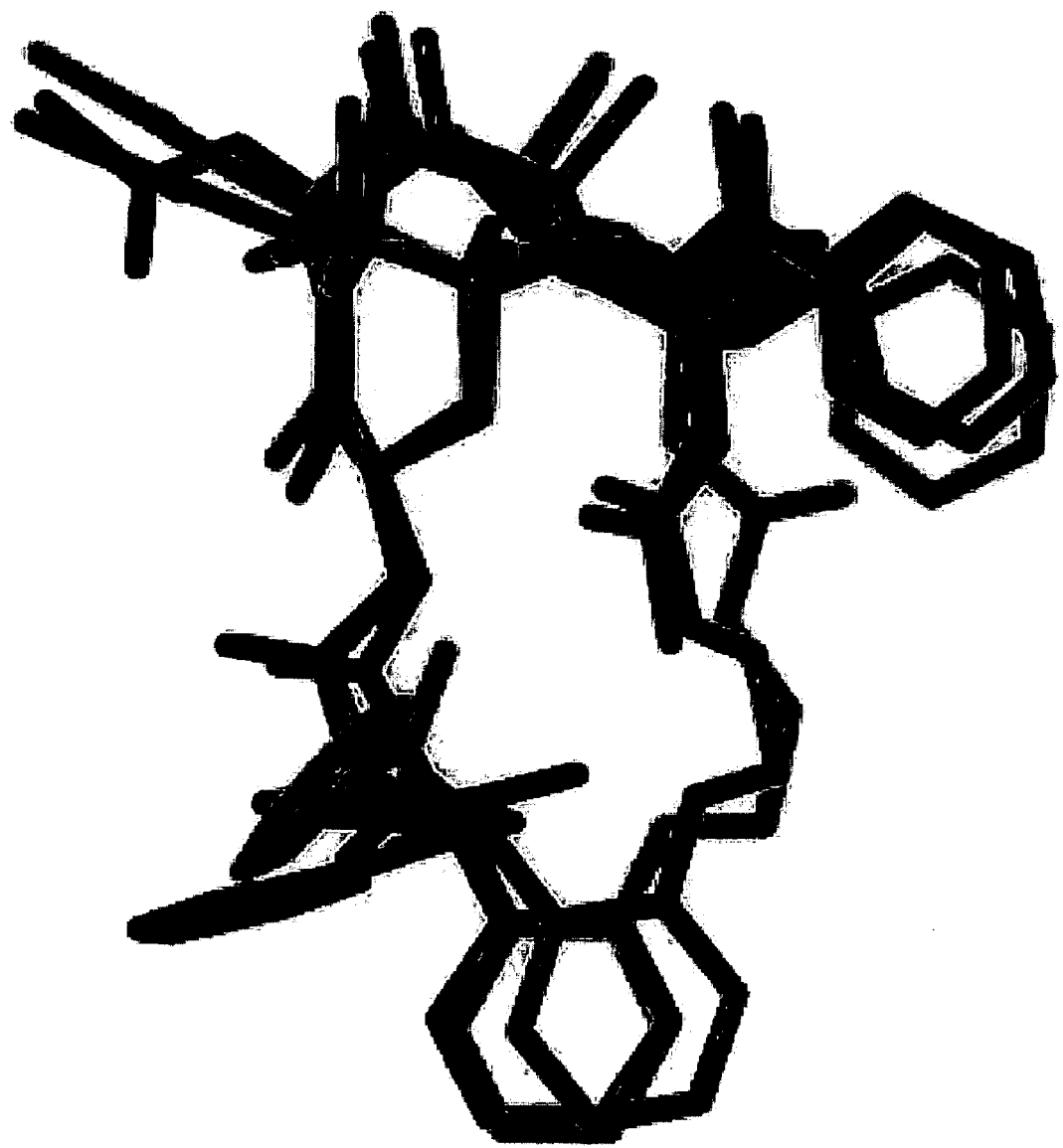
FIG. 15. NAMFIS-derived T-conformations for 13b (76% black, 7% light grey) superimposed on the tubulin-bound T-Taxol form (dark grey). As illustrated by FIG. 14, these conformations together comprise a total of 83% in the T-Taxol conformer proposed as the tubulin-bound form. The decreased torsional freedom and reduced molecular volume of ortho-bridged 13b contributes to its equipotency with Taxol relative to the more flexible, larger and less active meta-bridged 16.
Figure 16:
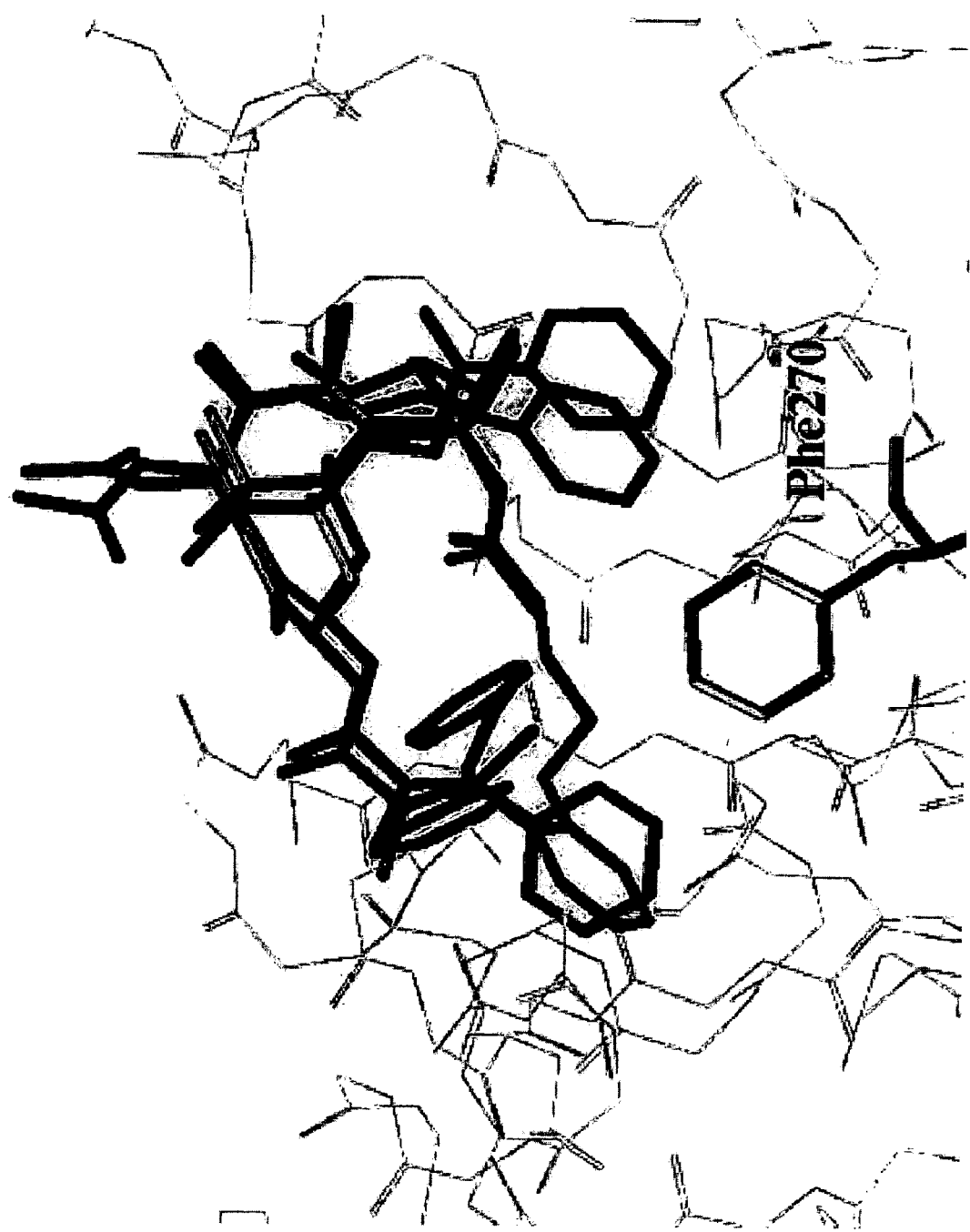
FIG. 16. T-Taxol bound to β-tubulin. The ortho-bridged T-form of 13b (both ligand and protein binding site subjected to MD relaxation similar to T-Taxol) superimposed on Taxol avoids the steric contact with Phe270 at the bottom of the hydrophobic taxoid pocket experienced by the meta-bridged analog 16.

$^a$Taxol has $IC_{50}$ values 6-15 nM in this assay.
$^b$Taxol has an average $IC_{50}$ value of 4 nM in this assay.
$^c$Tubulin concentration 5 $\mu M$.
$^d$Taxoid concentration 10 $\mu M$.
ND, not determined The induction of tubulin assembly by Taxol and related molecules is a function of both the affinity of the ligand for the Taxol binding site on tubulin and the effect of ligand binding on the conformation of the protein. These two parameters can be measured separately. The affinity of ligands for the Taxol binding site on microtubules can be determined by competition between the ligand in question and a radioactive or fluorescent derivative of Taxol. FIG. 14 shows that the binding of the fluorescent Taxol derivative N-AB-PT (15) to stabilized microtubules was inhibited to the same extent by Taxol and 13b, demonstrating that they bind to the Taxol site on microtubules with equal affinity. Single point assays for inhibition of N-AB-PT binding to tubulin by other Taxoids indicate that the relative affinities of the molecules for the Taxol binding site on tubulin are roughly parallel to their assembly promoting abilities and cytotoxicities.

Taxol binding to polymerized tubulin affects the conformation of the protein in a way that favors tubulin assembly, i.e., by increasing the equilibrium constant for polymer growth ($K_p$). The reciprocal of the critical concentration is a very close approximation of $K_p$. Table 1 shows the critical concentration for tubulin assembly in the presence of Taxol and the conformationally restricted Taxol analogs. All four molecules are at least as active as Taxol in lowering the critical concentration of tubulin, indicating that they are all effective promoters of the assembly-active conformation of tubulin.

It should be noted that two compounds with a bridge from the meta-position of the C-3'-phenyl group to the C-4OAc group were previously disclosed (B. B. Metaferia, J. Hoch, T. E. Glass, S. L. Bane, S. K. Chatteijee, J. P. Snyder, A. Lakdawala, B. Cornett, and D. G. I. Kingston, "Synthesis and Biological Evaluation of Novel Macrocyclic Paclitaxel Analogs." Org. Lett. 2001, 3, 2461-2464). These compounds differ in two significant ways from the compounds claimed in this disclosure. In the first place they are linked from the meta position rather than the ortho position of the C-3' phenyl; this linkage position causes an unfavorable interaction between the tether and Phe272 of the tubulin. As a consequence these compounds are significantly less active than PTX, with IC50 values for tubulin-assembly activities and cytotoxicities at least tenfold greater than those of PTX.

Ligand-Tubulin Structure: Solution Conformations by NMR/NAMFIS Analysis. In the initial approach to fitting the electron crystallographic density with conformational candidates, it was reasoned that a dataset of conformations determined by combining single crystal X-ray and solution NMR structures would prove to furnish more realistic binding candidates than a completely virtual docking approach. Thus, the NMR/NAMFIS method was employed to identify a low population Taxol conformation (4%, i.e. Taxol in either $CDCl_3$ or $D_2O/DMSO$-$d_6$ (Snyder, J. P.; Nevins, N.; Jiménez-Barbero, J.; Cicero, D.; Jansen, J. M. unpublished) displays eight and fourteen conformers, respectively) the populations of which are solvent dependent. T-Taxol appears in $CDCl_3$ and $D_2O/DMSO$-$d_6$ mole fractions of 0.04 (4%) and 0.02 (2%), respectively) that matched the electron crystallographic density on tubulin, namely T-Taxol. The meta-bridged compound 16 with less than one-tenth the activity of Taxol was similarly determined to exist in solution to the extent of 5%. According to the NAMFIS analysis, the considerably more constrained ortho-bridged compound 13b in $CDCl_3$ exhibits two related conformers with residues at the bottom of the ligand pocket as previously modeled for 16. Compounds 13a and 14a with one less bridge atom between the ortho position of the C3'-phenyl and the 4-OAc methyl introduce additional molecular rigidification while maintaining the T-Taxol conformation as determined by conformational analysis. Accordingly, respective cytotoxicities exceed those of Taxol by a factor of up to 20.

Analysis of the T-Taxol conformation has suggested a novel bridging strategy linking the C-4 OAc methyl and the C-3' phenyl group that locks the molecule into the T-Taxol geometry. Minireceptor evaluation predicted the ortho-bridged unsaturated esters 13a and 13b and the corresponding saturated analogs 14b and 14b to be at least equipotent to Taxol's action as microtubule stabilizers. Subsequent synthesis taking advantage of the olefin metathesis approach has led to both compounds, the NMR/NAMFIS analysis for 13b demonstrating that more than 80% of the compound adopts the T-Taxol conformation in solution. Tubulin polymerization and cytotoxicity assays are complementary by demonstrating for the first time that bridged taxoids, namely 13b and 14b, are capable of showing equivalence to Taxol in their biological action. The outcomes highlight three important conclusions to be drawn from our work.

First, the electron crystallographic-based modeling study that identified T-Taxol as the bioactive conformation would appear to be independently substantiated. By constraining the two C-3' and C-2 phenyl rings to be distant from one another (FIG. 13), the hydrophobically collapsed "polar" and "non-polar" conformations are eliminated as viable binding forms.

Figure 17:
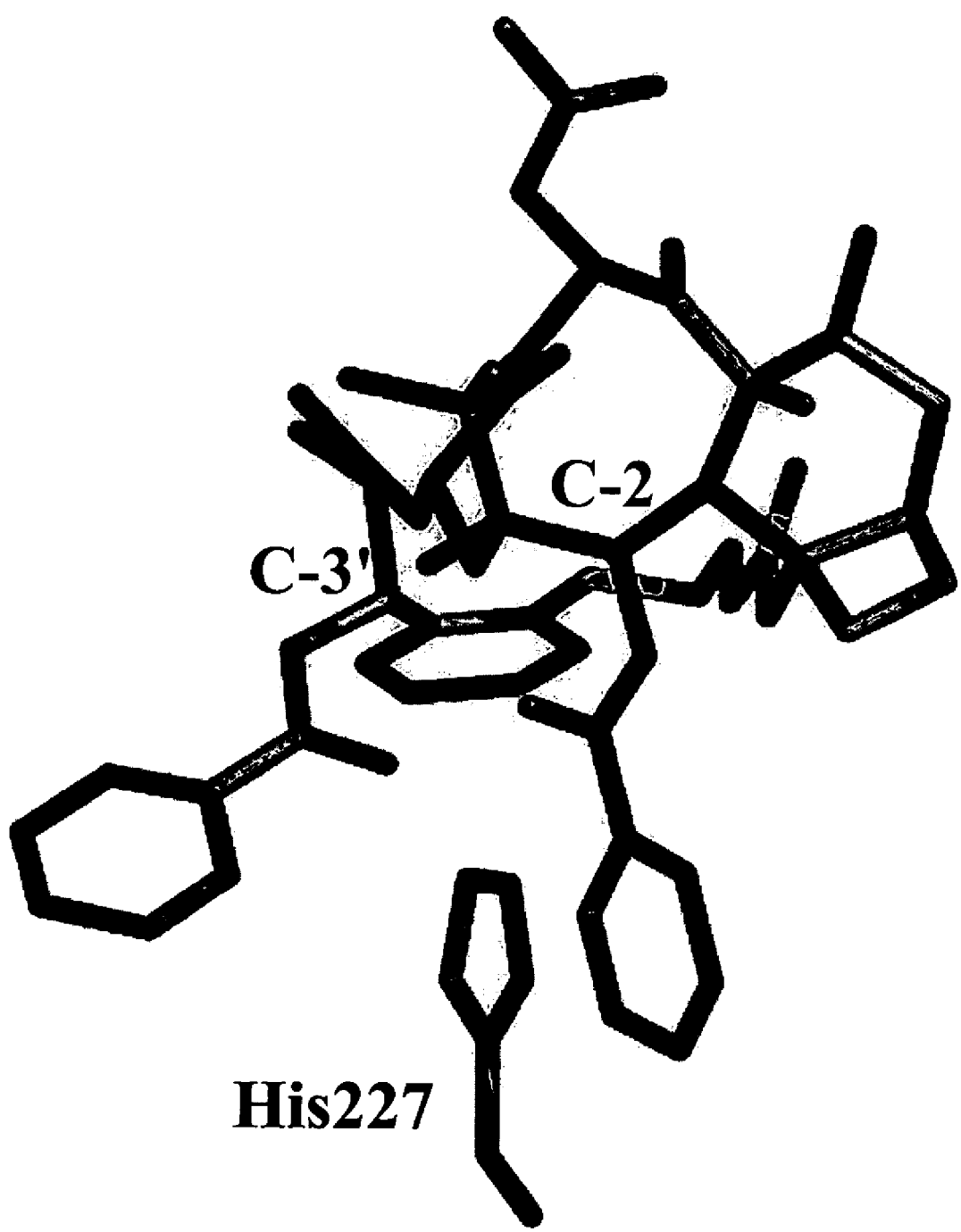
FIG. 17. A view of ortho-bridged 13b in which phenyl rings emanating from C-2 and C-3' surround the imidazole of His227 in a sandwich motif; the C-4 OAc to C-3' phenyl bridge avoids the latter while stabilizing the T-Taxol conformation.

The second point follows, which is that the present results contrast sharply with those derived by bridging from either the C-3' phenyl or the benzamido side chain directions to the C-2 position of the baccatin core; cases in which the activity is either nonexistent or at best one-tenth that of Taxol. The fundamental reason for activity in the present series and its absence in other bridging schemes is related to the location of β-tubulin's His227 in the taxoid binding pocket. This protein residue is part of a three-ring stacking motif in which its imidazole ring resides between the C-2 benzoyl and C-3' benzamido phenyl rings of Taxol. Consequently, most tethers connecting the C-3' and C-2 centers are unable to achieve the necessary arrangement. Compounds 13a/b and 14a/b, on the other hand, not only accommodate the His227-ligand interaction, but constrain the molecules to the bioactive conformation by bridging behind the stacked rings (FIG. 17).

Third, the electron crystallographic analyses are derived from zinc-stabilized tubulin sheets in which the α,β-tubulin protofilaments are antiparallel. This contrasts with the parallel arrangement of protofilaments in cellular microtubules. It has been argued that the difference implies T-Taxol derived from the former is inapplicable to the latter. The present results obviate this argument and support the earlier inference that the Taxol binding site in the tubulin dimer derived from zinc-stabilized sheets is unaltered in the microtubule structure. The orientation of T-Taxol in the tubulin binding site is different from what two of us proposed in an earlier paper based on measurements performed on colchicinoid/tubulin complexes assembled with a fluorescent Taxol analog. The Taxol binding site on the colchicine-tubulin-stathmin complex is now known to be different from that in the zinc-sheet structure of tubulin. The binding mode of Taxol we proposed is therefore likely to be different from that of Taxol in the tubulin conformation found in microtubules and zinc-sheets Finally, the T-Taxol design strategy evolved here, short rigid bridges from C-4 to C-3', will permit other bridged structures to likewise surpass the activity of parent Taxol. Also, significantly modified or truncated compounds designed around this principle will provide novel classes of active and easily synthesized anti-tumor agents.

Compound Synthesis

Synthesis of Protected Acrylic Acid Ester B. To a solution of A (1 g, 1.1 mmol) in tetrahydrofuran (THF) (6 ml) was added drop wise Lithium hexamethyldisilazide (LiHMDS) (1 M, 1.3 ml, 1.3 mmol, 1.2 eq) at 0° C. and the resulting solution was stirred for 45 min. Acryloyl chloride (0.123 ml, 1.54 mmol, 1.3 eq) was added to the above solution at 0° C. and stirred the reaction mixture for 3 h. Saturated NH$_4$Cl solution (10 ml) was added, two layers were separated, and the aqueous phase was extracted with ethyl acetate (50 ml×3). The combined organics were washed with water, brine, dried over Na$_2$SO$_4$ and concentrated. The crude on chromatography over silica gel with 4% ethyl acetate in hexane gave B as a white solid (550 mg, 52% yield, based on unrecovered starting material). $^1$HNMR (400 MHz, CDCl$_3$): d 8.18 (2H, d, J=8.4 Hz), 7.62 (1H, d, J=7.2 Hz), 7.49 (2H, t, J=8 Hz), 6.56 (1H, dd, J=17.4, 1.2 Hz), 6.25 (1H, dd, J=17.4, 10.5 Hz), 6.15 (1H, dd, J=10.5, 1.17 Hz), 5.76 (1H, d, J=7 Hz), 4.94 (2H, t, J=9.5 Hz), 4.58 (1H, m), 4.48 (1H, dd, J=10, 6.6 Hz), 4.30 (2H, ABq, J=11.2, 8.4 Hz), 3.98 (1H, d, J=6.8 Hz), 2.55 (1H, m), 2.30 (2H, m), 2.00 (3H, s), 1.98 (1H, m), 1.70 (3H, s), 1.22 (3H, s), 1.13 (3H, s), 1.0 (27H, m), 0.65 (18H, m), 0.05 (3H, d, J=2.7 Hz), -0.28 (3H, d, J=2.7 Hz). $^{13}$CNMR (100 MHz): d 205.6, 165.3, 164.4, 138.9, 135.7, 133.1, 130.6, 130.3, 130.1, 130.0, 128.3, 84.1, 82.1, 81.3, 75.9, 75.7, 72.7, 68.2, 58.3, 46.6, 44.0, 39.3, 37.4, 27.3, 21.3, 14.5, 10.4, 7.0, 6.9, 6.0, 5.2, 4.9, 4.8, 0.4, 0.05, High resolution fast atom bombardment mass spectroscopy (HRFABMS): Calculated for C$_{50}$H$_{85}$O$_{10}$Si$_4$ 957.5220, observed: 957.5202.

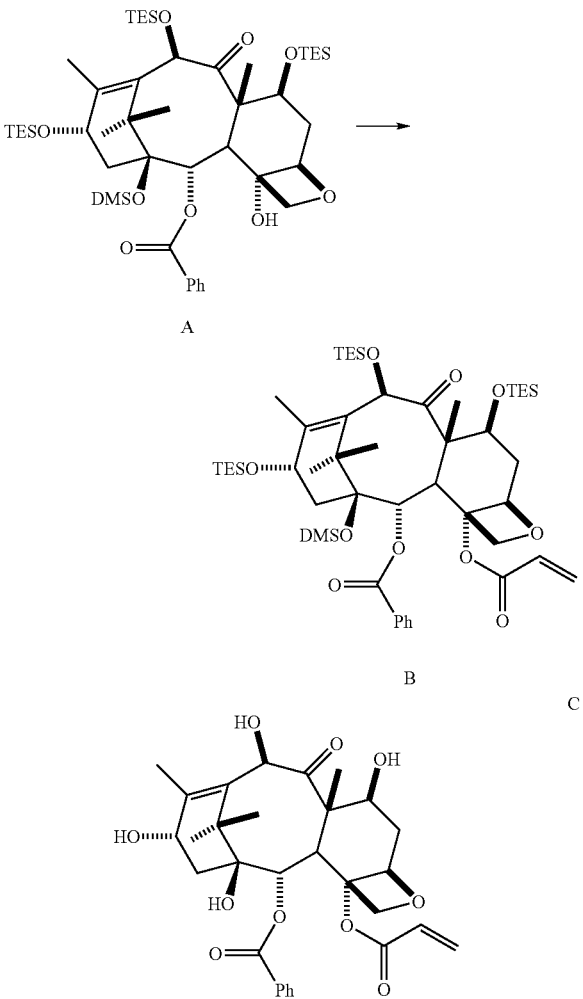

Deprotection of B. To a solution of B (470 mg, 0.49 mmol) in THF (30 ml) was added dropwise HF.Py (70% HF, 2.37 ml) at 0° C. and the resulting solution was brought to room temperature over 24 h. Saturated NaHCO$_3$ solution (50 ml) was added carefully to quench the reaction and two layers were separated. The aqueous phase was extracted with ethyl acetate (50 ml×3). The combined organics were washed with water, brine, dried over Na$_2$SO$_4$ and concentrated. The crude was subjected to silica gel preparative thin layer chromatography with 70% ethyl acetate in hexane to give C as white solid (193 mg, 70% yield). $^1$HNMR (400 MHz, Acetone-d$_6$): d 8.15 (2H, d, J=8.4 Hz), 8.00 (1H, s), 7.61 (1H, m), 7.55 (2H, m), 6.42 (1H, dd, J=17.4, 1.2 Hz), 6.28 (1H, dd, J=17.4, 10.5 Hz), 5.95 (1H, dd, J=10.5, 1.2 Hz), 5.67 (1H, d, J=7.2 Hz), 5.29 (1H, d, J=2.4 Hz), 4.95 (1H, d, J=8.4 Hz), 4.82 (1H, m), 4.44 (1H, m), 4.20 (3H, m), 4.15 (1H, t, J=4.8 Hz), 3.48 (1H, s), 2.85 (1H, s), 2.48 (1H, m), 2.29 (1H, m), 1.92 (1H, m), 1.74 (3H, s), 1.10 (3H, s), 1.06 (3H, s). $^{13}$CNMR (100 MHz): d 211.0, 165.9, 164.8, 142.8, 134.9, 133.3, 130.8, 130.6, 130.0, 129.8, 129.5, 128.8, 128.7, 84.4, 81.1, 77.9, 76.2, 75.3, 75.1, 71.9, 67.2, 57.9, 47.3, 42.9, 40.3, 37.0, 26.6, 19.8, 14.7, 9.6. HRFABMS: Calculated for $C_{30}H_{37}O_{10}$: 557.2387, observed: 557.24001

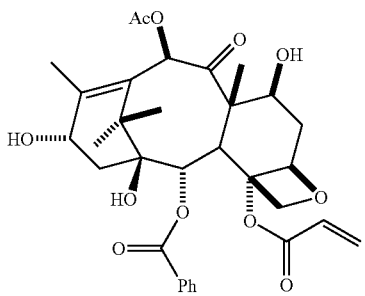

D

Synthesis of Baccatin III Acrylate D. To a solution of C (210 mg, 0.377 mmol) in THF (10 ml) was added anhydrous $CeCl_3$ (20 mg) and the resulting solution was stirred for 5 min. Acetic anhydride (0.65 ml, 14-fold excess) was added to the above solution and stirred the reaction mixture for 4 hrs. Ethyl acetate (100 ml) was added and washed with saturated $NaHCO_3$, water, brine, dried over $Na_2SO_4$ and concentrated. The crude was subjected to silica gel preparative thin layer chromatography with 60% ethyl acetate in hexane to give D as white solid (200 mg, 96% based on recovered starting material). $^1$HNMR (500 MHz, $CDCl_3$): d 8.0 (2H, d, J=8.4 Hz), 7.59 (1H, t, J=7 Hz), 7.46 (2H, t, J=8 Hz), 6.48 (1H, dd, J=17.4, 1.2 Hz), 6.32 (1H, s), 6.27 (1H, dd, J=17.4, 10.5 Hz), 6.00 (1H, dd, J=17.4, 1.2 Hz), 5.62 (1H, d, J=7 Hz), 4.96 (1H, dd J=9.6, 2 Hz), 4.79 (1H, t, J=7 Hz), 4.52 (1H, dd, J=10.9, 6.8 Hz), 4.33 (1H, d, J=8.4 Hz), 4.20 (1H, d, J=8.5 Hz), 3.94 (1H, d, J=6.8 Hz), 2.56 (1H, m), 2.20 (3H, s), 2.22-2.18 (1H, m), 2.03 (3H, s), 1.86 (1H, m), 1.67 (3H, s), 1.08 (3H, s), 1.07 (3H, s). $^{13}$CNMR (125 MHz): d 204.1, 186.2, 171.4, 167.0, 165.2, 146.6, 133.7, 131.7, 131.3, 130.1, 129.6, 128.6, 84.5, 81.2, 79.1, 76.5, 76.3, 75.0, 72.3, 68.0, 58.8, 46.1, 42.7, 39.2, 35.7, 27.0, 20.9, 15.5, 9.5. HRFABMS: Calculated for $C_{32}H_{39}O_{11}$: 599.2492, observed: 599.25018.

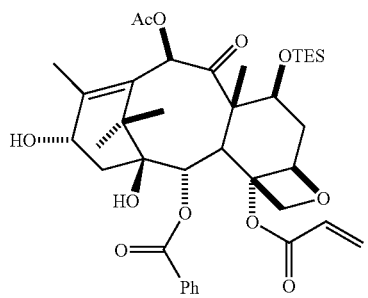

10

Synthesis of Triethylsilyl (TES) Protected Acrylate 10. To a solution of D (50 mg, 0.0836 mmol) in dichloromethane (5 ml) was added imidazole (56 mg, 0.836 mmol, 10 eq) followed by triethylsilylchloride (0.50 mmol, 6 eq) at 0° C. and the resulting solution was stirred for 3 h. Dilute hydrochloric acid (0.05M, 5 ml) solution was added to quench the reaction followed by ethyl acetate (40 ml). The organic phase was washed with water, brine, dried over $Na_2SO_4$ and concentrated. The crude was subjected to silica gel preparative thin layer chromatography with 45% ethyl acetate in hexane to give 10 as white solid (40 mg, 72% yield). $^1$HNMR (500 MHz, $CDCl_3$): d 8.11 (2H, d, J=7.1 Hz), 7.59 (1H, t, J=7.2 Hz), 7.46 (2H, t, J=7.2 Hz), 6.52 (1H, dd, J=17.4, 1.2 Hz, 1H), 6.47 (1H, s), 6.28 (1H, dd, J=17.4, 10.5 Hz), 6.01 (1H, dd, J=17.4, 1.2 Hz), 5.64 (1H, d, J=6.8 Hz), 4.94 (1H, d, J=7.7 Hz), 4.76 (1H, m), 4.53 (1H, dd, J=10, 6.7 Hz), 4.33 (1H, d, J=8.4 Hz), 4.20 (1H, d, J=8.4 Hz), 3.94 (1H, d, J=6.8 Hz), 2.55 (1H, m), 2.20 (3H, s), 2.22-2.10 (2H, m), 2.18 (3H, s), 1.90 (1H, m), 1.70 (3H, s), 1.18 (3H, s), 1.02 (3H, s), 0.91 (9H, t, J=7.2 Hz), 0.60 (6H, m). $^{13}$CNMR (125 MHz): d 202.2, 169.4, 165.3, 144.0, 133.7, 131.2, 130.1, 129.8, 129.6, 128.6, 84.2, 81.3, 78.8, 76.6, 75.8, 74.8, 72.4, 68.1, 58.8, 47.2, 42.8, 38.9, 37.3, 26.9, 21.0, 20.1, 14.9, 10.0, 6.84, 5.36. HRFABMS: Calculated for $C_{38}H_{53}O_{11}Si$: 713.3357, observed: 713.33258.

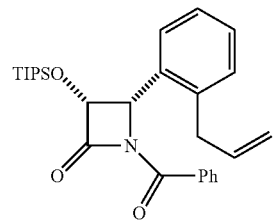

8a

Characterization Data for Compound 8a.

$[\alpha]_D$: +183.4 (c 0.35, $CHCl_3$). $^1$HNMR (400 MHz, $CDCl_3$): d 8.0 (2H, d, J=8 Hz), 7.60 (1H, t, J=7.2 Hz), 7.49 (2H, t, J=7.6 Hz), 7.37 (1H, m), 7.22 (3H, m), 6.05 (1H, m), 5.72 (1H, d, J=6.4 Hz), 5.31 (1H, d, J=6 Hz), 5.16 (1H, dd, J=11.6, 1.2 Hz), 5.12 (1H, dd, J=17, 1.6 Hz), 3.60 (2H, m), 1.0 (3H, m), 0.94 (18H, m). $^{13}$CNMR (100 MHz): d 166.4, 165.5, 138.5, 136.8, 133.5, 132.3, 132.1, 130.1, 129.8, 128.4, 128.3, 127.4, 126.3, 116.6, 76.7, 57.6, 37.6, 17.77, 17.74, 12.2. HRFABMS: Calculated for $C_{28}H_{38}NO_3Si$: 464.2621, observed: 464.2645.

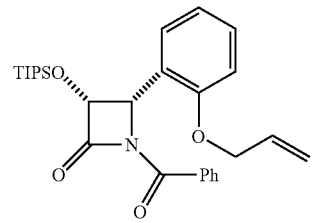

8b

Characterization Data for Compound 8b.

$[\alpha]_D$: +90 (c 0.7, $CHCl_3$). $^1$HNMR (500 MHz, $CDCl_3$): d 8.03 (2H, d, J=7.3 Hz), 7.56 (1H, t, J=7.3 Hz), 7.47 (2H, t, J=7.8 Hz), 7.29 (1H, dd, J=7.5, 1.6 Hz), 7.24 (1H, dd, J=7.6, 1.6 Hz), 6.94 (1H, t, J=7.6 Hz), 6.86 (1H, d, J=8.2 Hz), 6.07 (1H, m), 5.86 (1H, d, J=6.4 Hz), 5.40 (1H, dd, J=17.1, 1.6 Hz), 5.27 (1H, dd, J=10.5, 1.6 Hz), 5.26 (1H, d, J=6.2 Hz), 4.55 (2H, qd, J=13.4, 5 Hz), 1.0 (3H, m), 0.89 (18H, d, J=6.8 Hz). $^{13}$CNMR (125 MHz): d 166.4, 165.8, 157.0, 133.4, 133.2, 132.5, 129.9, 129.1, 128.2, 128.1, 122.3, 120.5, 117.6, 111.5, 76.8, 69.2, 57.2, 17.67, 17.62, 12.0. HRFABMS: Calculated for $C_{28}H_{38}NO_4Si$: 480.2570, observed: 480.2567.

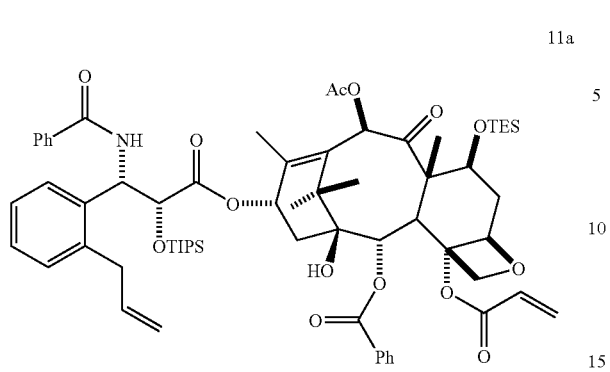

11a

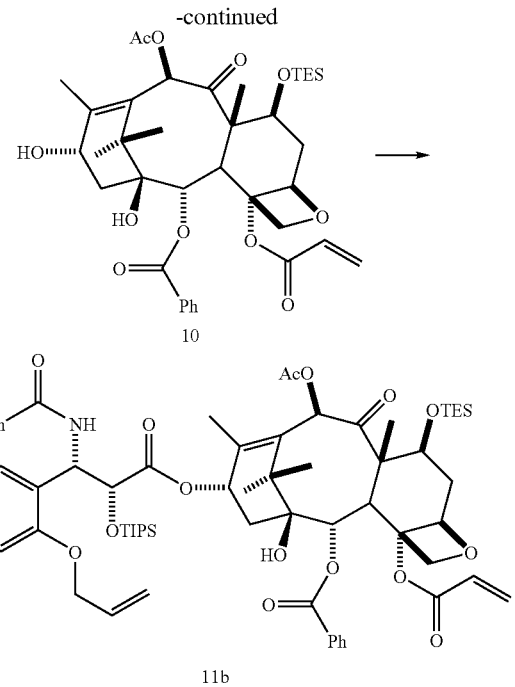

Characterization Data for Coupled Product 11a. Lactam 8a was coupled with baccatin III derivative 10 as described below for compound 11b. $^1$HNMR (400 MHz, CDCl$_3$): d 8.11 (2H, d, J=8 Hz), 7.70 (2H, d, J=7.6 Hz), 7.60 (1H, t, J=7.6 Hz), 7.44-7.52 (4H, m), 7.38 (2H, t, J=7.6 Hz), 7.24-7.31 (3H, m), 6.95 (1H, d, J=9.2 Hz), 6.48 (1H, s), 6.44 (1H, d, J=1.6 Hz), 6.32 (1H, d, J=10 Hz), 6.28 (1H, d, J=10 Hz), 6.0 (1H, m), 5.95 (1H, t, J=9.6 Hz), 5.80 (1H, d, J=9.6 Hz), 5.75 (1H, d, J=7.2 Hz), 5.57 (1H, dd, J=10, 1.6 Hz), 5.18 (1H, dd, J=16.8, 1.6 Hz), 5.12 (1H, dd, J=10, 1.6 Hz), 4.90 (1H, d, J=7.6 Hz), 4.74 (1H, d, J=1.6 Hz), 4.54 (1H, dd, J=10.4, 6.4 Hz), 4.34 (1H, d, J=8 Hz), 4.25 (1H, d, J=8.4 Hz), 3.90 (1H, d, J=7.2 Hz), 3.72 (1H, dd, J=15, 6.4 Hz), 3.52 (1H, dd, J=15.4, 6.8 Hz), 2.56 (1H, m), 2.40 (2H, m), 2.18 (3H, s), 2.03 (3H, s), 1.71 (3H, s), 1.23 (3H, s), 1.18 (3H, s), 1.00-1.07 (11H, m), 0.94 (9H, t, J=8 Hz), 0.60 (6H, m). $^{13}$CNMR (100 MHz): d 202.8, 172.8, 169.5, 167.0, 165.0, 140.9, 137.4, 136.8, 136.2, 134.3, 133.7, 133.5, 132.0, 131.8, 130.29, 130.23, 129.7, 129.4, 128.8, 128.8, 128.5, 127.7, 127.6, 127.0, 126.8, 117.3, 84.4, 81.7, 78.9, 75.2, 74.4, 73.4, 72.3, 58.6, 52.4, 46.9, 43.5, 37.4, 37.1, 36.1, 26.6, 21.8, 21.0, 18.2, 18.1, 14.4, 13.0, 10.3, 6.9, 5.5. HRFABMS: Calculated for C$_{60}$H$_{89}$NO$_{14}$Si$_2$Na: 1198.5719, observed: 1198.5742.

Synthesis of Coupled Product 11b. To a solution of NaH (35 mg, excess) in THF (2 ml) was added 10 (16 mg, 0.022 mmol) in THF (0.65 ml) at 0° C., and the resulting solution was stirred for 15 min. A solution of 8b (21 mg, 0.044 mmol, 2 eq) in THF (0.8 ml) was added to the above reaction mixture at 0° C. and the resulting solution was brought to room temperature over 24 h. Saturated NH$_4$Cl (2 ml) solution was added to quench the reaction followed by ethyl acetate (50 ml). The organic phase was washed with water, brine, dried over Na$_2$SO$_4$ and concentrated. The crude was subjected to silica gel preparative thin layer chromatography with 25% ethyl acetate in hexane to give 11b (13 mg, 50% yield, based on unrecovered starting material).

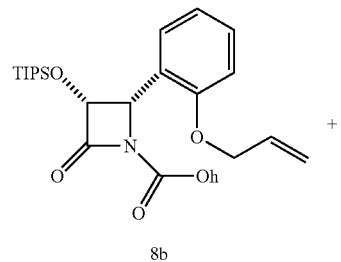

8b

11b

HNMR (500 MHz, CDCl$_3$): d 8.12 (2H, d, J=7.1 Hz), 7.73 (2H, d, J=7.1 Hz), 7.54 (1H, t, J=7.3 Hz), 7.44 (4H, m), 7.33 (2H, t, J=7.8 Hz), 7.27 (1H, m), 7.05 (1H, d, J=9 Hz), 6.94 (2H, m), 6.65 (1H, dd, J=17, 10 Hz), 6.57 (1H, dd, J=17.4, 1.2 Hz), 6.47 (1H, s), 6.35 (1H, m), 6.22 (1H, t, J=7.4 Hz), 5.95 (1H, dd, J=10, 1.2 Hz), 5.88 (1H, dd, J=10, 1.1 Hz), 5.68 (1H, d, J=7.3 Hz), 5.53 (1H, dd, J=17.4, 1.4 Hz), 5.35 (2H, 2 singlets), 4.90 (1H, d, J=7 Hz), 4.80 (1H, dd, J=7.4, 5 Hz), 4.60 (2H, m), 4.30 (1H, d, J=8.2 Hz), 4.21 (1H, d, J=8.2 Hz), 3.84 (1H, d, J=7.4 Hz), 2.55 (1H, m), 2.30 (1H, m), 2.17 (3H, s), 2.06 (3H, s), 1.98 (1H, m), 1.71 (3H, s), 1.65 (3H, s), 1.20 (3H, s), 1.06 (1H, m), 0.98 (27H, m), 0.60 (9H, m). $^{13}$CNMR (100 MHz): d 201.8, 172.4, 169.3, 166.3, 165.6, 155.4, 140.7, 138.5, 134.4, 133.4, 133.2, 132.8, 131.5, 130.2, 129.4, 129.0, 128.7, 128.6, 128.2, 126.9, 125.9, 121.1, 119.0, 111.5, 84.2, 80.8, 79.4, 77.2, 75.2, 74.9, 72.9, 72.3, 71.0, 69.4, 58.3, 53.2, 47.0, 43.3, 37.1, 36.0, 29.7, 26.7, 22.0, 20.9, 17.8, 14.2, 12.5, 10.0, 6.7, 5.3. HRFABMS: Calculated for C$_{66}$H$_{89}$NO$_{15}$Si$_2$Na: 1214.5668, observed: 1214.5667.

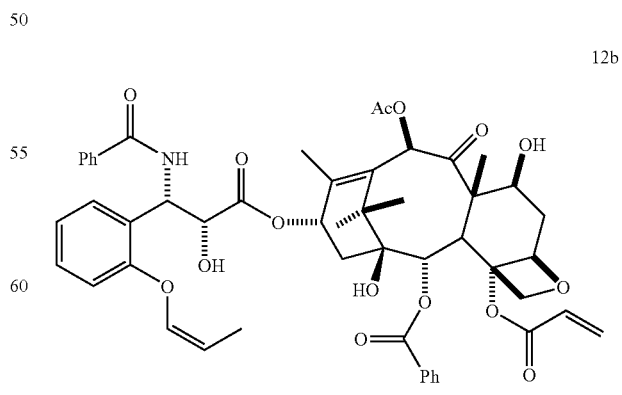

12b

Synthesis of Compound 12b. To a solution of 11b (10 mg, 0.0084 mmol) in THF (2 ml) was added drop wise HF.Py (70% HF, 0.15 ml) in pyridine (0.15 ml) at 0° C. and the resulting solution was brought to room temperature over 7 h. Saturated NaHCO$_3$ solution (5 ml) was added carefully to quench the reaction and two layers were separated. The aqueous phase was extracted with ethyl acetate (10 ml×3). The combined organics were washed with water, brine, dried over Na$_2$SO$_4$ and concentrated. The crude was subjected to silica gel preparative thin layer chromatography with 50% ethyl acetate in hexane to give 12b (6.3 mg, 81% yield). $^1$HNMR (400 MHz, CDCl$_3$): d 8.15 (2H, d, J=8 Hz), 7.75 (2H, d, J=8 Hz), 7.60 (1H, t, J=7 Hz), 7.51 (4H, m), 7.40 (3H, m), 7.05 (3H, m), 6.55 (1H, dd, J=17.4, 1.2 Hz), 6.40 (1H, dd, J=17.2, 10.4 Hz), 6.33 (1H, s), 6.15 (2H, m), 5.97 (1H, dd, J=9, 3.6 Hz), 5.82 (1H, dd, J=10.4, 1.2 Hz), 5.73 (1H, d, J=7.2 Hz), 5.55 (1H, dd, J=17.2, 1.2 Hz), 5.36 (1H, dd, J=10.6, 1.2 Hz), 4.98 (1H, d, J=7.6 Hz), 4.79 (1H, dd, J=6.4, 3.6 Hz), 4.72 (2H, dd, J=5.4, 1.6 Hz), 4.54 (1H, m), 4.37 (1H, d, J=8.4 Hz), 4.26 (1H, d, J=9.2 Hz), 3.88 (1H, d, J=7.2 Hz), 3.51 (1H, d, J=6.4 Hz), 2.60 (1H, m), 2.53 (1H, d, J=4 Hz), 2.36 (1H, dd, J=15.4, 8.8 Hz), 2.28 (3H, s), 2.24 (1H, dd, J=15.4, 8.8 Hz), 1.93 (1H, m), 1.89 (3H, s), 1.73 (3H, s), 1.28 (3H, s), 1.18 (3H, s). $^{13}$CNMR (100 MHz): d 204.0, 173.3, 171.5, 167.3, 167.1, 165.4, 156.1, 142.8, 134.2, 133.8, 133.0, 132.6, 132.5, 131.9, 130.3, 129.9, 129.5, 129.2, 129.0, 128.8, 127.2, 126.1, 121.6, 118.7, 112.5, 84.6, 81.4, 79.3, 77.4, 76.6, 75.8, 75.3, 72.8, 72.36, 72.31, 69.4, 58.7, 52.6, 45.8, 43.4, 35.9, 35.7, 29.9, 27.0, 22.2, 21.1, 15.0, 9.8. HRFABMS: Calculated for C$_{51}$H$_{56}$NO$_{15}$: 922.3650, observed: 922.36414.

Synthesis of Intermediates E-1 and E-2. To a solution of 11b (12 mg, 0.01 mmol) in dichloromethane (3 ml) was added Grubbs's second generation catalyst (3 mg, 0.003 mmol) in dichloromethane (2 ml) for 3 h, and the resulting solution was stirred for another 1 h. The reaction mixture was concentrated, and crude product was subjected to silica gel preparative thin layer chromatography with 26% ethyl acetate in hexane to give E-1 (7.5 mg, 64% yield). Compound E-2 was prepared similarly from 11a.

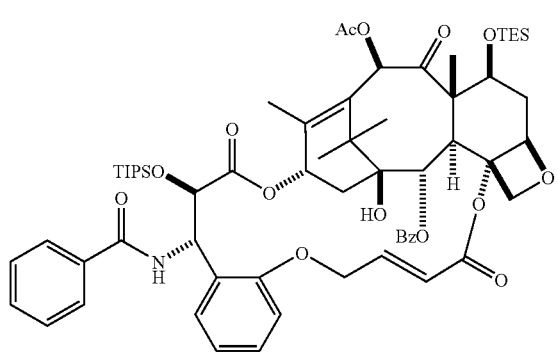

E-1

Characterization Data for E-1.
$^1$HNMR (500 MHz, CDCl$_3$): d 8.06 (2H, d, J=7.1 Hz), 7.75 (2H, d, J=7.1 Hz), 7.60 (1H, t, J=7.3 Hz), 7.48 (2H, m), 7.44 (2H, t, J=6 Hz), 7.32 (2H, m), 7.17 (1H, d, J=9 Hz), 7.0 (2H, m), 6.64 (1H, d, J=15.8 Hz), 6.45 (1H, s), 6.11 (1H, t, J=5.5 Hz), 5.81 (1H, d, J=8.9 Hz), 5.73 (1H, d, J=7 Hz), 5.14 (1H, s), 5.12 (1H, d, J=7.8 Hz), 4.84 (1H, ABq, J=10, 1 Hz), 4.83 (1H, ABq, J=10, 1 Hz), 4.48 (1H, d, J=8Hz), 4.46 (1H, d, J=8 Hz), 4.27 (1H, d, J=8.2 Hz), 3.78 (1H, d, J=6.8 Hz), 2.54 (2H, m), 2.16 (3H, s), 2.12 (1H, m), 2.0 (3H, s), 1.95 (1H, m), 1.70 (3H, s), 1.2 (3H, s), 1.14 (3H, s), 0.91 (30H, m), 0.5 (6H, m). $^{13}$CNMR (125 MHz): d 201.7, 172.8, 169.3, 167.6, 167.0, 164.7, 155.4, 141.9, 140.4, 134.2, 133.8, 133.6, 131.8, 130.0, 129.5, 129.2, 128.8, 128.7, 127.1, 127.0, 124.6, 122.8, 115.1, 83.8, 81.4, 78.9, 76.2, 75.2, 74.9, 73.3, 72.2, 67.8, 58.2, 52.6, 47.1, 43.4, 37.1, 35.7, 29.7, 26.5, 21.8, 20.9, 17.9, 17.7, 14.2, 12.4, 10.3, 6.8, 5.3. HRFABMS: Calculated for C$_{64}$H$_{86}$NO$_{15}$Si$_2$: 1164.5536, observed: 1164.5469.

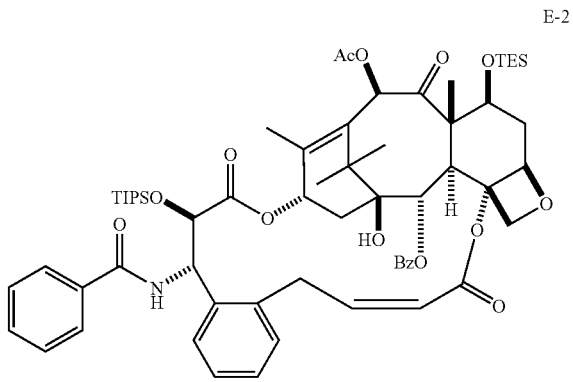

E-2

Characterization Data for E-2.
$^1$HNMR (400 MHz, CDCl$_3$): d 8.13 (2H, d, J=7.8 Hz), 7.78 (2Hd, J=7.1 Hz, 2H), 7.58 (t, J=7.3 Hz, 1H), 7.5 (m, 3H), 7.38-7.42 (m, 3H), 7.23-7.31(m, 3H), 6.72(td, J=10, 2.8 Hz, 1H), 6.5 (s, 1H), 6.41 (t, J=8 Hz 1H) 6.30(dd, J=11.2, 1.6 Hz, 1H), 5.74 (d, J=4.4 Hz, 1H), 5.78 (d, J=3.2 Hz, 1H), 5.01(d, J=8 Hz,1H), 4.86(dd, J=20, 9.2 Hz, 1H), 4.67 (d J=0.8 Hz, 1H), 4.46(dd, J=10.4, 7.8 Hz, 1H), 4.33(d, J=8 Hz, 1H), 4.24 (d, J=8.4 Hz, 1H), 3.82 (d, J=6.4 Hz, 1H) 3.67(dt, 19.2, 3.2 Hz, 1H), 2.6 (m, 1H), 2.21 (m, 1H), 2.20 (s, 3H), 2.08(m, 1H), 2.05 (s, 3H), 1.99 (m, 1H), 1.75 (s, 3H), 1.26 (s, 3H), 1.24 (s, 3H), 0.94(m, 30H), 0.6 (m, 6H). $^{13}$CNMR (100 MHz): d 202, 171.4, 169.6, 167.3, 166.6, 165.1, 153.3, 140.5, 138.2, 137.2, 134.1, 133.9, 133.5, 132.0, 130.7, 130.4, 129.2, 128.9, 128.5, 127.5, 127.16, 127.10, 120.6, 84.2, 81.1, 78.8, 75.4, 74.8, 74.4, 72.9, 70.6, 59.2, 53.5, 47.0, 43.8, 37.9, 35.7, 34.9, 29.9, 27, 21.4, 21.1, 18.2, 17.9, 14.9, 12.9, 10.2, 7.0, 5.5. HRFABMS: Calculated for C$_{64}$H$_{85}$NO$_{14}$Si$_2$Na: 1170.5406, observed: 1170.5426.

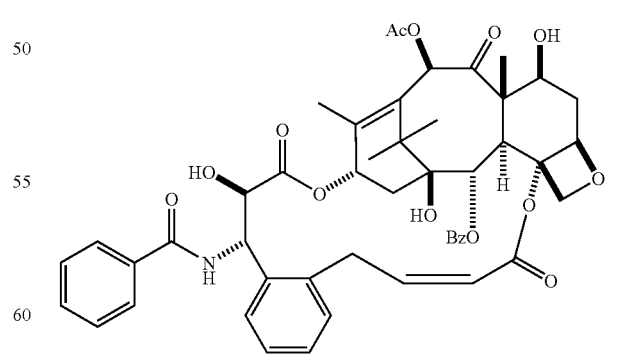

13a

Characterization Data for 13a.
$[a]_D$: −66.6 (c 0.09, CHCl$_3$). $^1$HNMR (400 MHz, CDCl$_3$): d 8.14 (d, J=8 Hz, 2H), 7.76 (d, J=7.6 Hz, 2H), 7.60 (t, J=7.2 Hz, 1H), 7.42-7.52 (m, 6H), 7.30 (m, 3H), 7.13 (d, J=8 Hz, 1H), 6.76 (td, J=9.2, 2 Hz, 1H), 6.49 (t, J=8.8 Hz 1H) 6.36 (s, 1H), 6.30 (dd, J=11.4, 2 Hz, 1H), 5.93 (d, J=8 Hz, 1H), 5.73 (d, J=6.8 Hz, 1H), 5.01 (d, J=7.6 Hz, 1H), 4.89 (dd, J=19.2, 9.2 Hz, 1H), 4.46 (d, J=9.2 Hz, 1H), 4.35 (s, 1H), 4.34 (d, J=8.4 Hz, 1H), 4.24 (d, J=8 Hz, 1H), 3.89 (d, J=6.8 Hz, 1H), 3.66 (td, J=19.2, 2.8 Hz, 1H), 3.25 (d, J=2 Hz, 1H), 2.66 (m, 1H), 2.48 (m, 2H), 2.24 (s, 3H), 2.24-2.26 (m 1H), 1.94-1.96 (m, 1H), 1.95 (s, 3H), 1.75 (s, 3H), 1.3 (s, 3H), 1.19(s, 3H). $^{13}$CNMR (100 MHz): d 203.8, 173.3, 171.4, 167.3, 166.8, 165.6, 153.2, 142.4, 138.6, 137.0, 134.0, 133.3, 132.1, 131.0, 130.5, 129.2, 129.0, 128.9, 128.6, 127.9, 127.3, 126.5, 120.5, 84.6, 81.3, 79.2, 75.7, 75.0, 72.9, 72.6, 72.2, 59.1, 51.0, 46.2, 43.6, 36.3, 35.6, 35.1, 27.2, 22.0, 21.0, 15.5, 9.7. HRFABMS: Calculated for $C_{49}H_{52}NO_{14}$: 878.3388, observed: 878.33820.

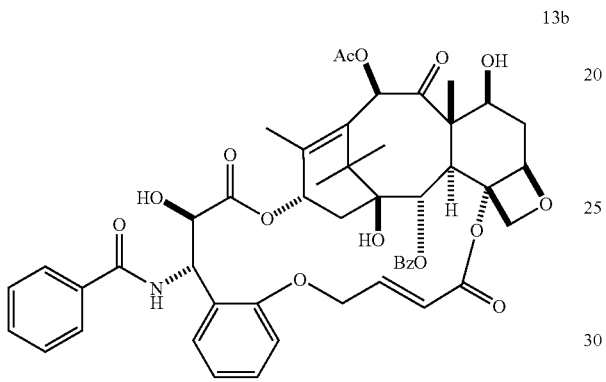

13b

Synthesis of 13b. To a solution of E-1 (7.5 mg, 0.006 mmol) in THF (2 ml) was added HF.Py (70%, 0.1 ml) at 0° C. and the resulting solution was brought to room temperature for 12 h. Saturated NaHCO$_3$ solution (10 ml) was added carefully to quench the reaction followed by ethyl acetate (10 ml×3) extraction. The combine ethyl acetate was washed with water, brine, dried over Na$_2$SO$_4$ and concentrated. The crude was subjected to silica gel preparative thin layer chromatography with 60% ethyl acetate in hexane to give 13b (5.6 mg, 98% yield. [a]$_D$: −72 (c 0.2, CHCl$_3$). $^1$HNMR (500 MHz, CDCl$_3$): d 8.10 (d, J=7.1 Hz, 2H), 7.72 (d, J=7.1 Hz, 2H), 7.60 (t, J=6.5 Hz, 1H), 7.52 (m, 3H), 7.40 (t, J=6 Hz, 1H), 7.35-7.28 (m, 4H), 7.11 (d, J=7.8 Hz, 1H), 7.05 (m, 1H), 6.66 (d, J=15.5 Hz, 1H), 6.26 (s, 1H), 6.15 (t, J=5.5 Hz 1H) 5.98 (d, J=7.75 Hz, 1H), 5.69 (d, J=7 Hz, 1H), 5.08 (d, J=7.5 Hz, 1H), 4.97 (ABq, J=10, 1 Hz, 1H), 4.87 (ABq, J=10, 1 Hz, 1H), 4.76 (t, J=4.1 Hz), 4.46 (m, 1H), 4.45 (d, J=8.4 Hz, 1H), 4.26(d, J=8.45 Hz, 1H), 3.74 (d, J=7.3 Hz, 1H), 3.19 (bs, 1H), 2.56 (m, 1H), 2.47 (d, J=4 Hz, 1H), 2.23 (s, 3H), 1.92 (m, 1H), 1.86 (s, 3H), 1.68 (s, 3H), 1.22 (s, 3H), 1.12(s, 3H). $^{13}$CNMR (125 MHz): d 203.7, 173.9, 171.4, 167.2, 167.1, 164.9, 155.4, 142.5, 142.3, 133.9, 133.8, 133.2, 132.0, 130.1, 129.5, 129.4, 128.8, 127.0, 125.1, 123.3, 116.1, 84.1, 81.3, 79.4, 76.1, 75.5, 75.4, 72.9, 72.4, 72.1, 58.3, 45.9, 43.3, 35.7, 35.3, 29.7, 26.8, 22.6, 20.9, 14.7, 9.8. HRFABMS: Calculated for $C_{49}H_{52}NO_{15}$: 894.3337, observed: 894.3343.

NMR/NAMFIS Analysis for 13b

Monte Carlo conformational analysis of 13b using the MMFF force field and an aqueous continuum solvation model (GBSA/H$_2$O) in MACROMODEL 6.5 yielded 858 fully optimized conformations. Separately, the 400 MHz rotating frame Overhauser Effect Spectroscopy (ROESY) analysis of 13b in CDCl$_3$ delivered 17 intramolecular distances. These were coded into the NMR analysis of molecular flexibility in solution (NAMFIS) program as follows, where the numbers refer to atom numbering for the structures in the conformational data set.

```
nameToIndexMap = {
    "H2prim" : 93,
    "H3prim" : 90,
    "H7" : 96,
    "H10" : 91,
    "H2" : 97,
    "Me16" : (104, 105, 106),
    "Me19" : (110, 111, 112),
    "Me18" : (98, 99, 100),
    "H6a" : 86,
    "H6b" : 87,
    "H13" : 92,
    "Me17" : (107, 108, 109),
    "H3" : 94,
    "H20a" : 88,
    "H20b" : 89,
    "H5" : 95,
    "OpH3m" : 73,
    "OCH2_1" : 82,
    "OCH2_2" : 83,
    "OpH3o" : 79,
    "Halpha" : 80,
    "OpH2o1" : 74,
    "OpH2o2" : 75,
    "3pNH" : 113,
}
permutations = [
    ("H6a", "H6b"),
    ("H20a", "H20b"),
    ("OpH2o1", "OpH2o2"),
]
noeDistances = [
    {"groups" : ("H2prim", "H3prim"), "distance" : 2.5},
    {"groups" : ("H7", "H10"), "distance" : 2.1},
    {"groups" : ("H3", "H10"), "distance" : 2.4},
    {"groups" : ("H2", "Me17"), "distance" : 2.1},
    {"groups" : ("H2", "Me19"), "distance" : 2.2},
    {"groups" : ("H10", "Me18"), "distance" : 2.0},
    {"groups" : ("H7", "H6a"), "distance" : 2.6},
    {"groups" : ("H13", "Me16"), "distance" : 2.7},
    {"groups" : ("H3", "Me18"), "distance" : 2.5},
    {"groups" : ("H20a", "Me19"), "distance" : 2.2},
    {"groups" : ("H5", "H6a"), "distance" : 3.1},
    {"groups" : ("H3", "H7"), "distance" : 2.6},
    {"groups" : ("H3", "Me19"), "distance" : 3.3},
    {"groups" : ("OpH3o", "OCH2_1"), "distance" : 2.1},
    {"groups" : ("OpH3o", "OCH2_2"), "distance" : 2.1},
    {"groups" : ("H2prim", "Halpha"), "distance" : 2.6},
    {"groups" : ("OpH2o1", "3pNH"), "distance" : 2.6},
]
```

Execution of NAMFIS produced a "best fit" of the 858 conformers and the 17 ROESY distances. The calculation results in three conformations in CDCl$_3$, two of which differ by torsions in the C-4 to C-3' bridge, but correspond to the T-Taxol form for a total of 83% (60.6+15.5+6.7%). NAMFIS conformers 1 and 3 (i.e. 789 and 774 in the conformer dataset, respectively) are the same C13-side chain conformer (60.6+15.5=76.1%), differing only in the rotation of the Cl—OH bond. The explicit NAMFIS output follows:

Bridge CH2 [1,2]—o-ring

Best fit run on 858 conformers.

SSD=80.79

Conformers with non-zero populations:

| | | |
|---|---|---|
| 1 | Conf # 789 | 60.6% - T-conf |
| 2 | Conf # 760 | 17.2% - other |
| 3 | Conf # 774 | 15.5% - T-conf |
| 4 | Conf # 326 | 6.7% - T-conf |

789,760,774,326

Example 2

The diterpenoid paclitaxel (Taxol®) (1) first reported by Wall in 1971 emerged from being a laboratory curiosity in the 1970's and 1980's to a drug of major clinical importance in the 1990's, and it is currently used for the treatment of breast and ovarian cancers and for AIDS-related Kaposi's sarcoma. It is also used or under investigation for the treatment of a wide variety of other cancers. It is currently one of the largest selling anticancer drugs in history, with combined annual sales of it and its semisynthetic analog docetaxel (Taxotere®) (2) of well over 1 billion.

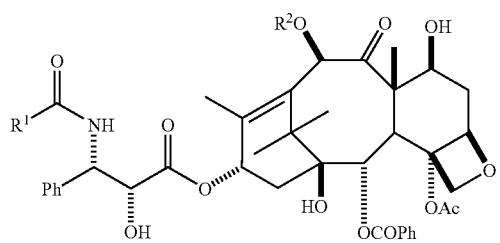

1 $R^1$ = Ph, $R^2$ = Ac
2 $R^1$ = Me$_3$CO, $R^2$ = H

Paclitaxel's importance as an anticancer drug has spurred a large amount of work on its chemistry and mechanism of action. In the chemistry area virtually every position on the ring and on the side chain has been subjected to structural modifications. The work described in these reviews has led to the development of several analogs of paclitaxel, which are in clinical trial as second-generation taxanes.

It would be highly desirable if future generations of this class of drugs could be structurally much simpler than paclitaxel, while retaining the full activity of the parent compound. The rational design of such simplified molecules requires a clear understanding of the tubulin-binding conformation of the parent molecule. The binding conformation was initially proposed as the T-taxol conformation on the basis of NAMFIS experiments and this conclusion has recently been established by the synthesis of macrocyclic taxol analog 3 which adopts the T-taxol conformation and which is significantly more active than paclitaxel.

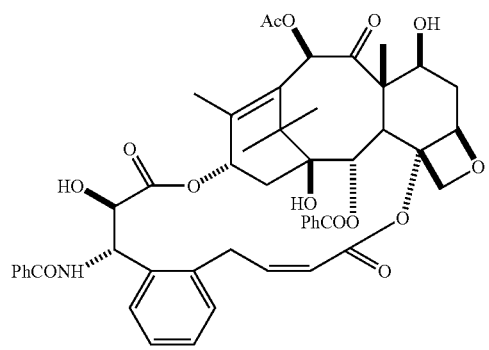

The bridged analog 3 defines the required conformation for the effective binding of paclitaxel analogs to tubulin. Based on this analysis, and also on the results of SAR studies which indicate that modifications to the northern hemisphere of paclitaxel do not cause significant detriment to its bioactivity, we have designed simplified paclitaxel analogs of general structure 4, by deleting the baccatin core of taxol and replacing it with a hydrophobic bicycle[3.3.1.]nonane moiety. The design, synthesis, and preliminary biological investigation of these model compounds is described in this communication.

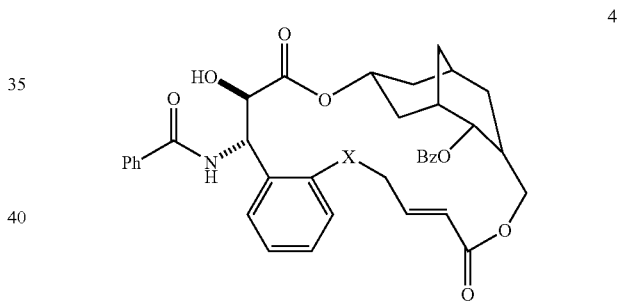

Scheme 1.
Synthesis of Baccatin III Analog 14.

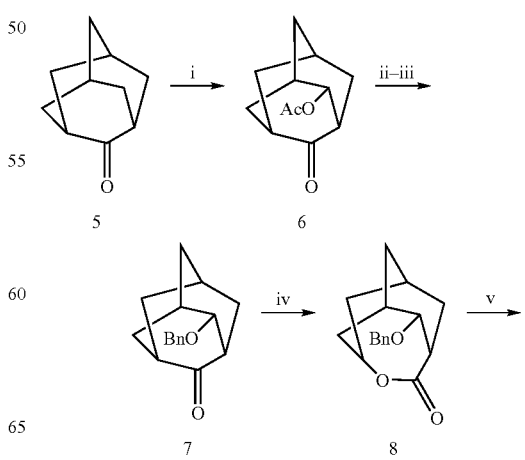

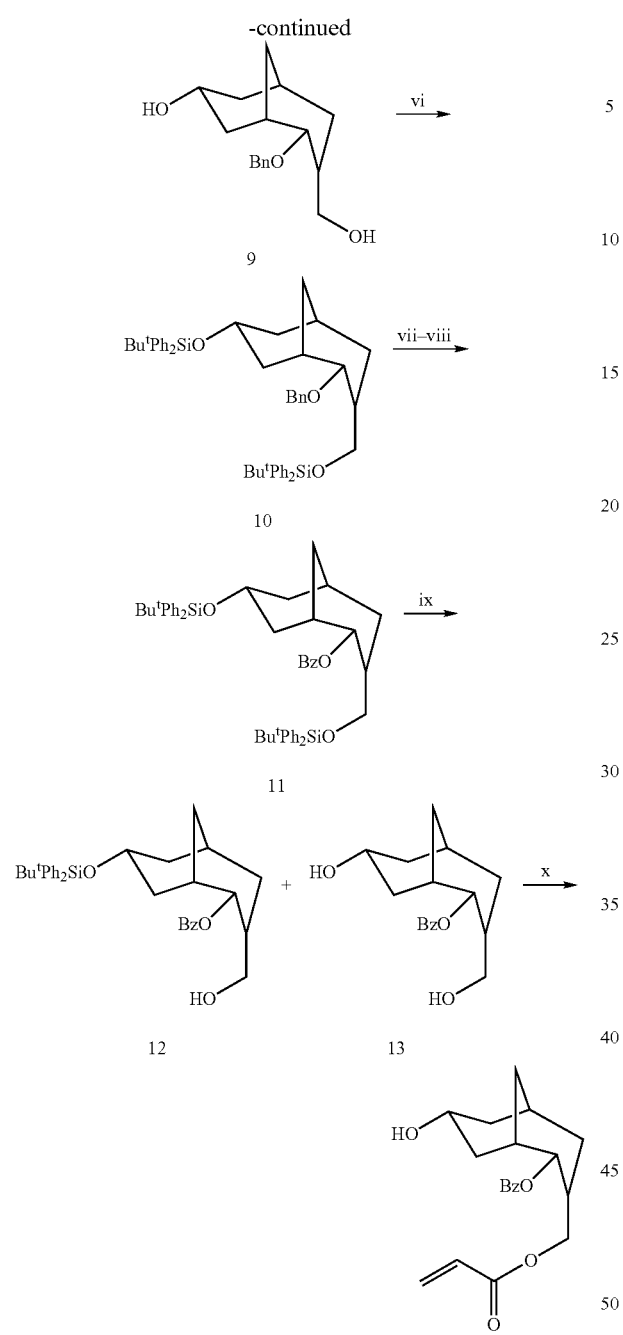

Scheme 1: Reagents and conditions: i. NaN₃, H₂SO₄, Ac₂O, (57%). ii. KOH, THF (85%). iii. NaH, BnBr, THF (95%). iv. AC₂O, AcOH, H₂O₂ (77%). v. LAH, THF (76%). vi. TBDPSCI, Imidazole, DMF, (92%). vii. Pd(OH)₂/C, 50Psi, 24 h, THF, (90%), viii. BzCl, Et₃N, DMAP, CH₂Cl₂ (95%) based on SM recovered. ix. HF-Pyridine, THF, 0° C.-RT, (70%). x. LHMDS, Acroylyl chloride, THF.

The synthesis of the 4 was achieved starting from commercially available 2-adamantanone 5 (Scheme 1). Adamantanone 5 was acetoxylated regioselectively to give acetoxy derivative 6. The acetyl functional group was then converted to a benzyl protected hydroxyl group to give 7. Baeyer-Villiger oxidation of 7 with Ac₂O: AcOH and H₂O₂ produced one product 8 regioselectively. Compound 8 was reduced with LiAlH₄ to provide diol 9 with satisfactory yields. Preliminary attempts to selectively protect one hydroxyl group of 9 failed to give monoprotected alcohol, and the bis (tert-butyldiphenyl)silyl ether 10 was formed even when ᵗBuPh₂SiCl was used with imidazole as catalyst. Bis silyl ether 9 was robust enough to survive hydrogenolysis in the presence of H₂—Pd(OH)₂/C at 50 psi, which conditions were used to deprotect the benzyl protecting group. The resulting free hydroxyl group was rebenzoylated with benzoyl chloride and triethylamine to give the benzoyl bis silyl ether 11. Deprotection of 11 gave the monodeprotected alcohol 12 and the diol 13 in a 1:4 ratio. Initial attempts to acylate diol 13 with acryloyl chloride using Li, Na, or KHMDS or BuLi failed to produce any desired product 13. This difficulty was circumvented by the use of EDCI coupling conditions using acrylic acid in the presence of DMAP to produce the acryloyl derivative 14. It is worth mentioning that the monoprotected alcohol 12 under similar EDCI conditions did not produce any desired product.

The synthesis of β-lactams 14a-d (Scheme 2) was carried out by standard methods, as previously described.

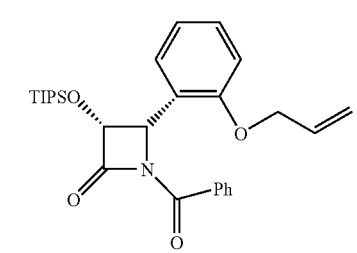

14a

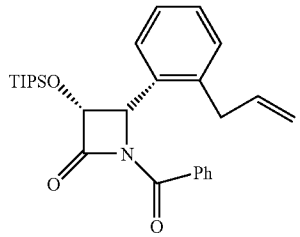

14b

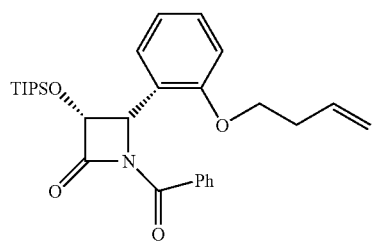

14c

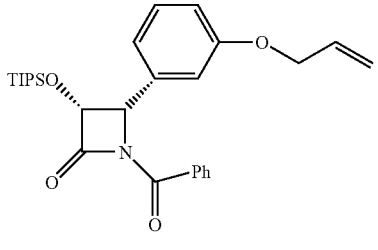

14d

With the building blocks 14 and 15a-d in hand, the crucial coupling was carried out using sodium hydride, and resulted the formation of the four sets of diastereomers 16a-d and 17a-d in nearly a 1:1 ratio. The pure individual compounds could be separated by chromatography. Each diastereomer was subjected to a ring closing metathesis reaction using Grubbs' second generation catalyst to produce the triisopropylsilyl protected macrocyclic derivatives. Deprotection of triisopropylsilyl ethers generated the simplified taxol like molecules 18a-c and 19a-c (Scheme-2). In the paclitaxel series (4) the double bond in the bridge had the E configuration, but these compounds were obtained in both Z (18a-b, 19a-b) and E (18c, 19c) configurations. The configurations were assigned based on NMR coupling constraints (J=8.4-8.8) Hz, J=15.6 Hz, for protons of the Z and E bridges, respectively).

Scheme 2.
Synthesis of Compounds 18 and 19

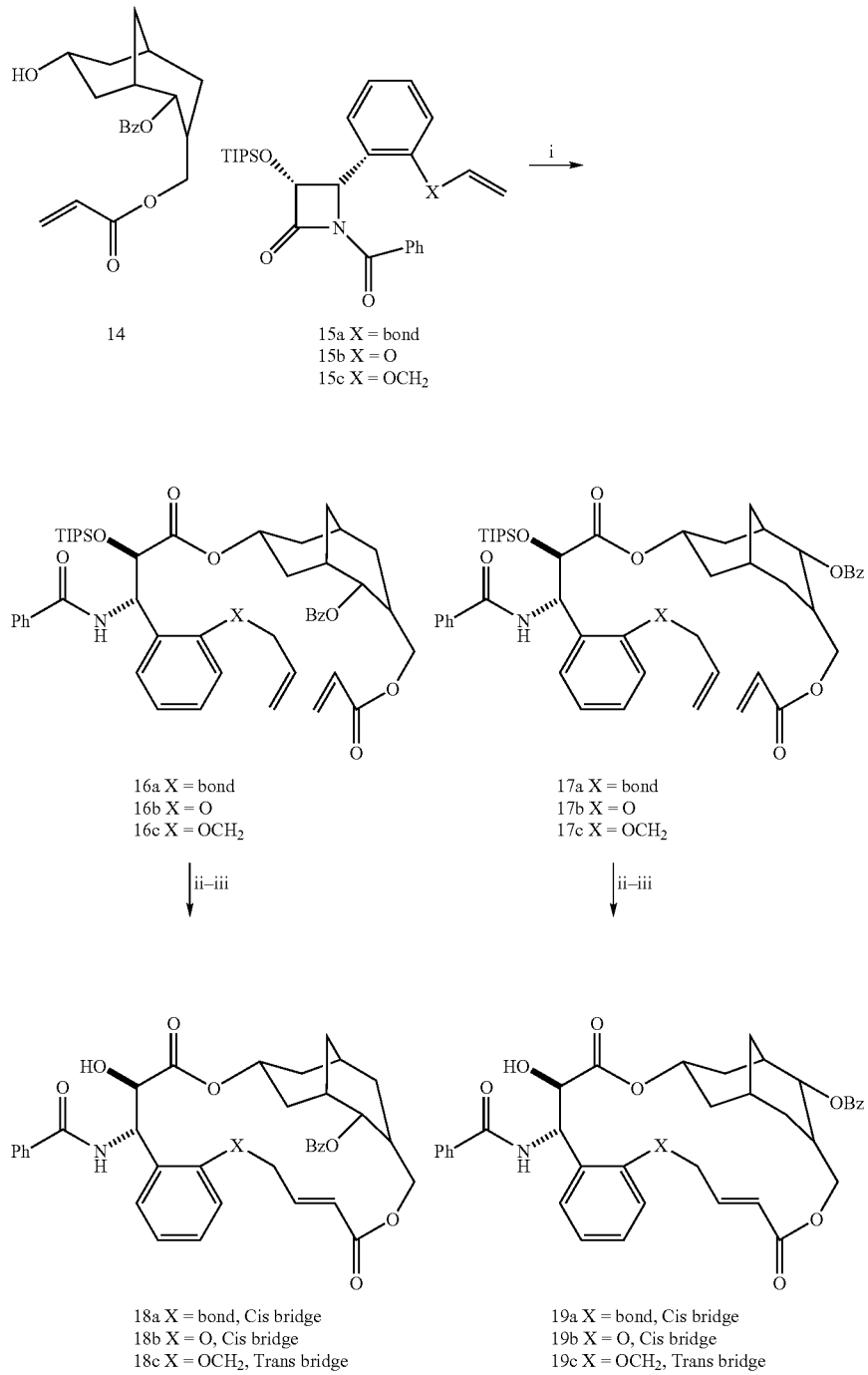

Reagents and conditions:
i. NaH, THF, 0° C.-RT,
ii.((Cy$_3$)P)(H$_2$IMes)Cl$_2$Ru=CHPh, CH$_2$Cl$_2$.
iii. HF-Pyridine, THF.

The compounds 20a-b were synthesized by a similar procedure starting from 14 and β-lactam 15d; in this case the E isomers were obtained.

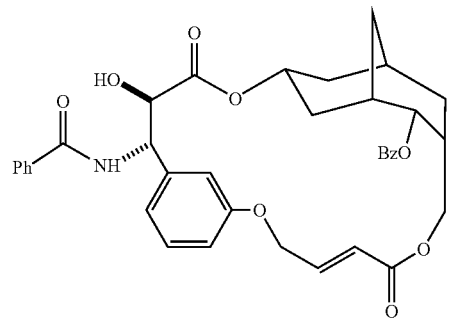

20a

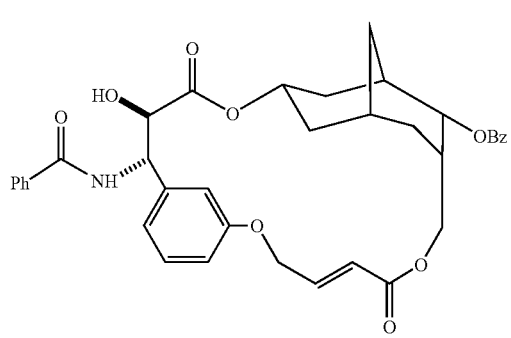

20b

Cytotoxicity determinations of compounds 18a-c and 19a-c were performed against the A2780 ovarian cell line and PC-3 prostate cell line. All the compounds were cytotoxic, but were significantly less active than taxol. However to the best of our knowledge, these are the completely simplified taxol like molecules with any such cytotoxicity. The cytotoxicity data for compounds 20a and 20b showed that these compounds were less active than 18 and 19.

Gratifyingly when these molecules were tested for their ability to assemble purified tubulin, compounds 18b and 19b exhibited significant tubulin polymerization activity, with about 10% of the activity of paclitaxel. Compounds 18c and 19c also showed modest activity (Table-1 for Example 2).

In summary some simple compounds that retain the T-taxol conformation have been designed. Synthesis and biological evaluation of these compounds provided model compounds that exhibit cytotoxicity and tubulin polymerization activity. The design strategy disclosed here has provided a new class of cytotoxic paclitaxel-like molecules. Incorporation of polar functional groups in the structures to make them water-soluble may increase their bioactivity.

TABLE 1 for Example 2.
Bioactivity of paclitaxel and analogs 18–20

| Compound | Cytotoxicity (IC$_{50}$, μg/ml) A2780 | Tubulin polymerization IC$_{50}$, μg/ml PC-3 |
| --- | --- | --- |
| Paclitaxel | 0.02 | |
| 18a | 12 | |
| 18b | 13 | |
| 18c | 8 | |

TABLE 1-continued for Example 2.
Bioactivity of paclitaxel and analogs 18–20

| Compound | Cytotoxicity (IC$_{50}$, μg/ml) A2780 | Tubulin polymerization IC$_{50}$, μg/ml PC-3 |
| --- | --- | --- |
| 19a | 8 | |
| 19b | 19 | |
| 19c | 19 | |
| 20a | >100 | |
| 20b | >100 | |

[a]Mean of three determinations
[b]Mean of two determinations

While the invention has been described in terms of its preferred embodiments, those skilled in the art will recognize that the invention can be practiced with modification within the spirit and scope of the appended claims.

Having thus describe our invention, what we claim as new and desire to secure by Letters Patent is as follows:

1. A pharmaceutical composition, comprising:
at least one paclitaxel derivative which includes a bridge from the C-3' position of the side chain to the C-4 position of a taxane skeleton which has the structures below

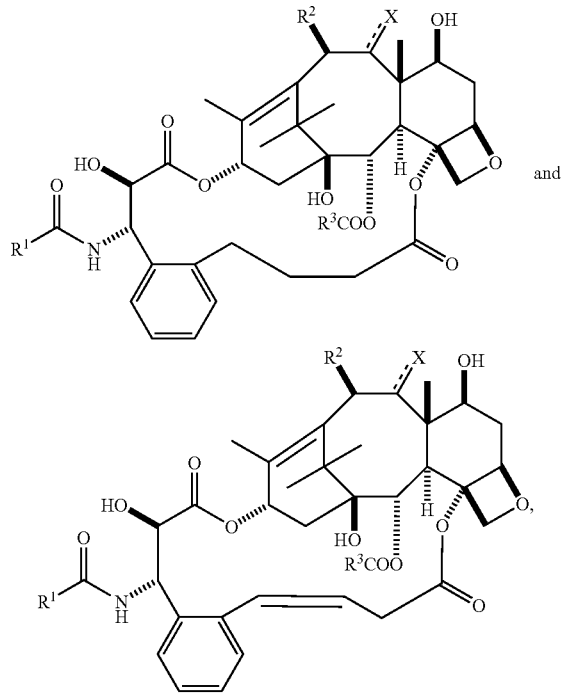

wherein
X is selected from the group consisting of O, CH$_2$, S, NH, OH and NH$_2$;
R$^1$ is selected from the group consisting of C$_1$ to C$_{10}$ linear or branched chain alkyl, alkenyl, and alkoxy groups, and substituted and unsubstituted aryl and heteroaryl rings;

$R^2$ is selected from the group consisting of hydrogen, OH, and OCOR$^4$, where R$^4$ is a C$_1$ to C$_{10}$ linear or branched chain alkyl, alkenyl, or alkoxy group; and $R^3$ is selected from the group consisting of methyl, a C$_1$ to C$_{10}$ linear or branched chain alkyl or alkenyl group, and an aryl or heteroaryl group;

an emulsifying agent; and a solvent.

2. A method for treating human cancer, comprising the step of administering to a patient in need thereof at least one paclitaxel derivative which includes a bridge from the C-3' position of the side chain to the C-4 position of a taxane skeleton, which has the structures below

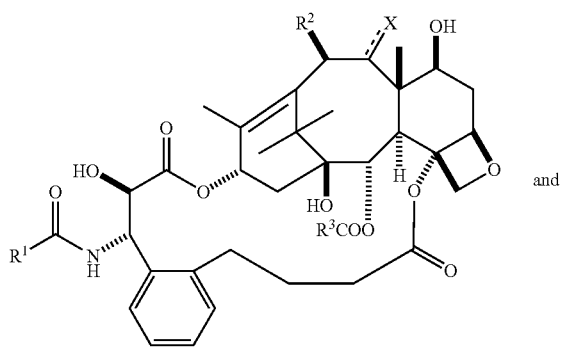

and

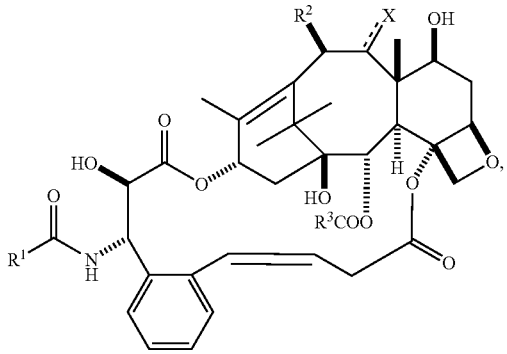

wherein

X is selected from the group consisting of O, CH$_2$, S, NH, OH and NH$_2$;

$^1$ R is selected from the group consisting of C$_1$ to C$_{10}$ linear or branched chain alkyl, alkenyl, and alkoxy groups, and substituted and unsubstituted aryl and heteroaryl rings;

R$^2$ is selected from the group consisting of hydrogen, OH, and OCOR$^4$, where R$^4$ is a C$_1$ to C$_{10}$ linear or branched chain alkyl, alkenyl, or alkoxy group; and R$^3$ is selected from the group consisting of methyl, a C$_1$ to C$_{10}$ linear or branched chain alkyl or alkenyl group, and an aryl or heteroaryl group.

3. The method of claim 2 wherein said paclitaxel derivative is administered in combination with an emulsifying agent and an alcohol.

4. The method of claim 2, wherein said human cancer is selected from the group consisting of breast cancer, ovarian cancer, and lung cancer.

5. The pharmaceutical composition of claim 1, wherein said solvent is an alcohol.

* * * * *